United States Patent
Kojima et al.

(10) Patent No.: US 8,684,046 B2
(45) Date of Patent: Apr. 1, 2014

(54) PUNCTURE REPAIR KIT

(75) Inventors: Yoshihide Kojima, Kobe (JP); Wen San Chou, Tainan Hsien (TW); Takaaki Ishida, Kobe (JP)

(73) Assignees: Sumitomo Rubber Industries, Ltd., Kobe (JP); Unik World Ind. Co., Ltd., Tainan (TW)

( * ) Notice: Subject to any disclaimer, the term of this patent is extended or adjusted under 35 U.S.C. 154(b) by 0 days.

(21) Appl. No.: 13/508,005

(22) PCT Filed: Oct. 20, 2010

(86) PCT No.: PCT/JP2010/068452
§ 371 (c)(1),
(2), (4) Date: Sep. 24, 2012

(87) PCT Pub. No.: WO2011/055633
PCT Pub. Date: May 12, 2011

(65) Prior Publication Data
US 2013/0138146 A1 May 30, 2013

(30) Foreign Application Priority Data

| Nov. 4, 2009 | (JP) | 2009-253259 |
| Nov. 4, 2009 | (JP) | 2009-253260 |
| Nov. 4, 2009 | (JP) | 2009-253261 |
| Nov. 4, 2009 | (JP) | 2009-253263 |
| Nov. 4, 2009 | (JP) | 2009-253264 |

(51) Int. Cl.
*B65B 31/00* (2006.01)
*B29C 73/16* (2006.01)

(52) U.S. Cl.
CPC ................... *B29C 73/166* (2013.01)

USPC .............. 141/38; 141/383; 152/415; 81/15.6

(58) Field of Classification Search
USPC ..................... 141/38, 67, 329–330, 382–383; 81/15.6; 152/415
See application file for complete search history.

(56) References Cited

U.S. PATENT DOCUMENTS 6,668,875 B2 * 12/2003 Kojima et al. .................. 141/38
6,786,247 B1 * 9/2004 Kemppainen et al. .......... 141/84
(Continued)

FOREIGN PATENT DOCUMENTS

| JP | 2000-108215 A | 4/2000 |
| JP | 2008-000896 A | 1/2008 |

(Continued)

*Primary Examiner* — Timothy L Maust
*Assistant Examiner* — Timothy P Kelly
(74) *Attorney, Agent, or Firm* — Birch, Stewart, Kolasch & Birch, LLP

(57) ABSTRACT

A puncture repair kit has a bottle unit positioned with greater stability. A puncture repair kit includes a compressor device, and a bottle unit in which a cap is attached to an opening in a bottle container which houses a puncture sealing agent. The compressor device includes a compressed air discharge port. The cap includes an air intake port for feeding compressed air from the compressed air discharge port into the bottle container, and a sealing agent/compressed air removal port for removing puncture sealing agent and compressed air in succession from the bottle container by feeding in compressed air. When the cap of the bottle unit is oriented downwards, the air intake port is directly connected with the compressed air discharge port. When this direct connection is made, the basal plane of the cap and the basal plane of the compressor device are flush with each other.

20 Claims, 32 Drawing Sheets

(56) References Cited

U.S. PATENT DOCUMENTS

| | | | |
|---|---|---|---|
| 7,178,564 B2 * | 2/2007 | Kojima et al. | 141/38 |
| 7,694,698 B2 * | 4/2010 | Marini | 141/38 |
| 7,789,112 B1 * | 9/2010 | Wise | 141/95 |
| 8,016,002 B2 * | 9/2011 | Yoshida et al. | 141/38 |
| 8,020,588 B2 * | 9/2011 | Wang | 141/38 |
| 8,201,586 B2 * | 6/2012 | Yoshida et al. | 141/38 |
| 8,205,645 B2 * | 6/2012 | Dowel | 141/38 |
| 8,276,624 B2 * | 10/2012 | Steele et al. | 141/38 |
| 2008/0145245 A1 * | 6/2008 | Chou | 417/415 |
| 2010/0189575 A1 | 7/2010 | Yoshida et al. | |
| 2013/0000777 A1 * | 1/2013 | Kojima et al. | 141/38 |
| 2013/0092286 A1 * | 4/2013 | Chou | 141/38 |
| 2013/0105055 A1 * | 5/2013 | Chou | 152/416 |

FOREIGN PATENT DOCUMENTS

| | | |
|---|---|---|
| JP | 2008-307861 A | 12/2008 |
| JP | 2009-226891 A | 10/2009 |
| JP | 2009-226892 A | 10/2009 |

* cited by examiner

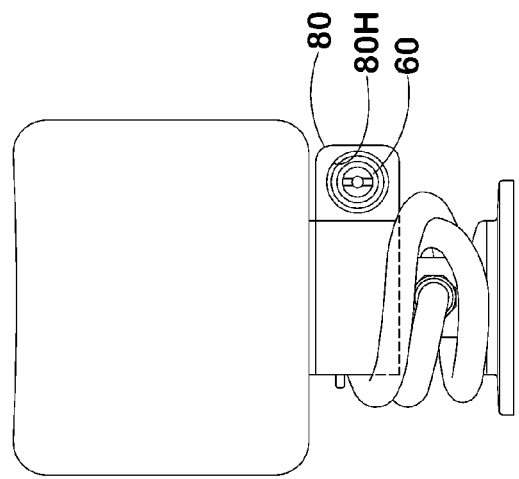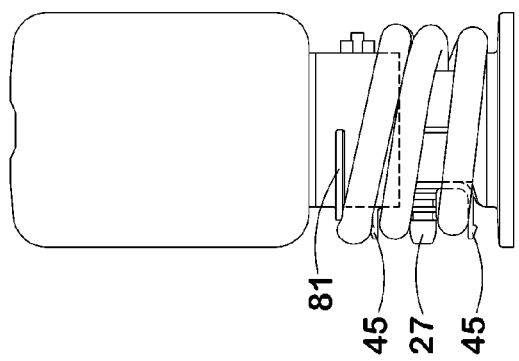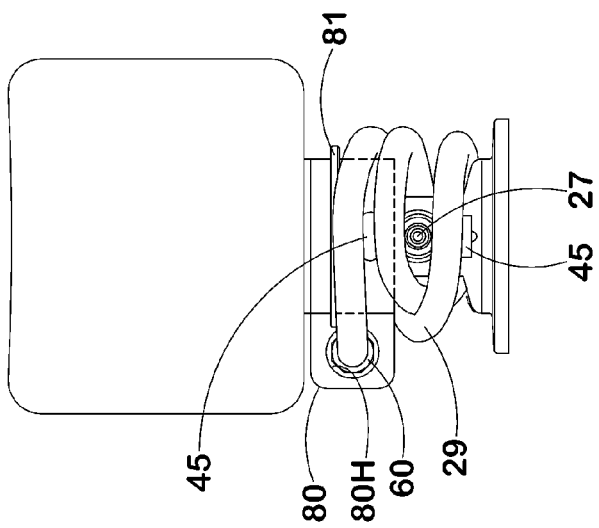

PUNCTURE REPAIR KIT

TECHNICAL FIELD

The present invention relates to a puncture repair kit for tire to inject puncture sealing agent and compressed air in succession into a punctured tire and to repair a puncture as an emergency procedure.

BACKGROUND OF THE INVENTION

An example of a puncture repair kit for repairing a puncture as an emergency procedure is the following patent document 1. Into a puncture tire, puncture sealing agent and compressed air are injected in succession, and the punctured tire is pumped up. And then, in this state, owing to roll the tire, the puncture sealing agent covers a whole circumference of a cavity surface of the tire so as to seal the puncture hole as an emergency procedure.

Such a repairing kit, as shown in FIG. 32, comprises a compressor device (a), and a bottle unit (d) comprising a bottle container (b) enclosing puncture sealing agent and a cap (c) attached to an opening of this bottle container (b). The above-mentioned cap (c) comprises an air intake port c1 to intake the compressed air from the above-mentioned compressed air discharge port into the bottle container (b), and a sealing agent/compressed air removal port c2 to remove in succession the puncture sealing agent and the compressed air from the above-mentioned bottle container (b) by sending this compressed air. The above-mentioned air intake port c1 is connected with an air supply hose e1 from the compressor device (a). The sealing agent/compressed air removal port c2 is connected with a second end of a feeding hose e2 of which first end is connected with the air valve of the tire T.

Patent Document 1: Japanese Unexamined Patent Application Publication No. 2000-108215.

DISCLOSURE OF THE INVENTION

Problems to be Solved by the Invention

This repair kit is necessary to be used in an inverted upright state of a bottle unit (d). However, because
 a. the bottle unit (d) is a tall,
 b. in a standpoint from a storage behavior, it is difficult to set the diameter of a basal plane of the cap (c) forming a foot to large enough, and
 c. a lateral force acts owing to push of the hoses e1 and e2 since the hoses e1 and e2 are connected,
it is liable to fall easily off the bottle unit (d) at work. So, it deteriorates a workability of the puncture repairing.

It is an object of the present invention to provide a puncture repair kit capable of improving stability of the bottle unit, and preventing a fall of the bottle unit, on a basis of directly connecting a compressor device with the bottle unit on a first side surface of the compressor device without hose and the like intervention, and in the directly connecting state, a basal plane of a cap and a basal plane of the compressor device are flush with each other.

Means for Solving the Problem

To solve the above-mentioned problems, the present application provides a puncture repair kit comprising a compressor device containing in a housing
  a motor and
  a compressor main body comprising
    a piston connected to the motor via a crank mechanism, and
    a cylinder reciprocatingly enclosing the piston and forming a pump chamber to compress the air between the cylinder and the piston, and
  a bottle unit comprising
    a bottle container enclosing puncture sealing agent and
    a cap attached to an opening of this bottle container.

The above-mentioned compressor device comprises a compressed air discharge port to discharge compressed air.

The above-mentioned cap comprises
  an air intake port to intake the compressed air from the above-mentioned compressed air discharge port into the bottle container, and
  a sealing agent/compressed air removal port to remove in succession the puncture sealing agent and the compressed air from the above-mentioned bottle container by sending this compressed air.

The above-mentioned compressor device has a shape of a flat rectangular box with a low height.

The above-mentioned air intake port of the above-mentioned bottle unit is directly connected with the above-mentioned compressed air discharge port disposed on a first side surface of the compressor device in an inverted state with the cap faced downward.

In the above-mentioned directly connecting state, the basal plane of the above-mentioned cap and the basal plane of the compressor device are flush with each other.

Effect of the Invention

In the present embodiment, as above stated, the bottle unit is directly connected on the first side surface of the compressor device. This bottle unit becomes therefore unified with the compressor device so as to have a lower center of gravity point. Moreover, the bottle unit is not connected with any air supply hose from the compressor device, and it becomes not to be affected by the power from the air supply hose. Moreover, the above-mentioned directly connecting state, i.e., the basal plane of the cap and the basal plane of the compressor device being flush with each other, increases a ground contacting area. Therefore, the present application improves stability and greatly and considerably improves fall-prevention efficacy of the bottle unit. Also, a conventional hose of the air intake port is not needed; it can prevent a pipe arrangement error.

BRIEF DESCRIPTION OF THE DRAWINGS

FIGS. 25 (A) to (C): A front view, a side view, and a back view showing the wrapping state of the feeding hose.

EXPLANATION OF THE REFERENCE

| | |
|---|---|
| 1 | Puncture repair kit |
| 2 | Compressor |
| 2S | Basal plane |
| 3 | Bottle unit |
| 4 | Bottle container |
| 5 | Opening |
| 6 | Cap |
| 6S | Basal plane |
| 7 | Sealing agent/compressed air removal port |
| 8 | Compressed air discharge port |
| 8a | Outlet port |
| 9 | Housing |
| 10 | Piston |
| 11 | Pump chamber |
| 12 | Cylinder |
| 13 | Compressor main body |
| 14a1 | First side surface |
| 16 | Dust-proof cap |
| 17 | Crank mechanism |
| 25 | Cylindrical portion |
| 25H | Central hole |
| 27 | Air intake port |
| 28 | Joint concave portion |
| 29 | Feeding hose |
| 30 | Trunk portion |
| 30A | Long side part |
| 30B | Short side part |
| 31 | Basal plate |
| 31A | Board portion |
| 32 | Bottle attaching part |
| 32A | Attaching concave part |
| 32B | Boss portion |
| 33 | Waist portion |
| 34A | Locking device |
| 35 | Air flow passage |
| 35a | Vertical air flow passage |
| 35a1 | Squeezing part |
| 35b | Horizontal air flow passage |
| 36 | Sealing agent/compressed air removal flow passage |
| 37 | Air flow passage upper opening |
| 38 | Sealing agent/compressed air removal flow passage upper opening |
| 39 | Sealing agent container |
| 41 | Connecting nozzle |
| 45 | Locking click |
| 50 | Circumscribed cuboid |
| 51 | Circumscribed cuboid |
| 54 | Cap portion |
| 55 | Ring securing part |
| 56 | Joining section |
| 60 | Connector |
| 80H | Rewinding-preventing hole |
| 80 | Rewinding-preventing plate portion |
| 81 | Guide rib |
| 95 | Side locking click |
| 95a | Projecting portion |
| 96 | Anterior locking click |
| 97 | Concave portion for receiving basal plate |
| 99 | Locking portion |
| M | Motor |
| Tv | Pressure release valve |

DETAILED DESCRIPTION OF THE INVENTION

Hereinafter, preferred embodiments of the present invention will be concretely described.

Figure 1:
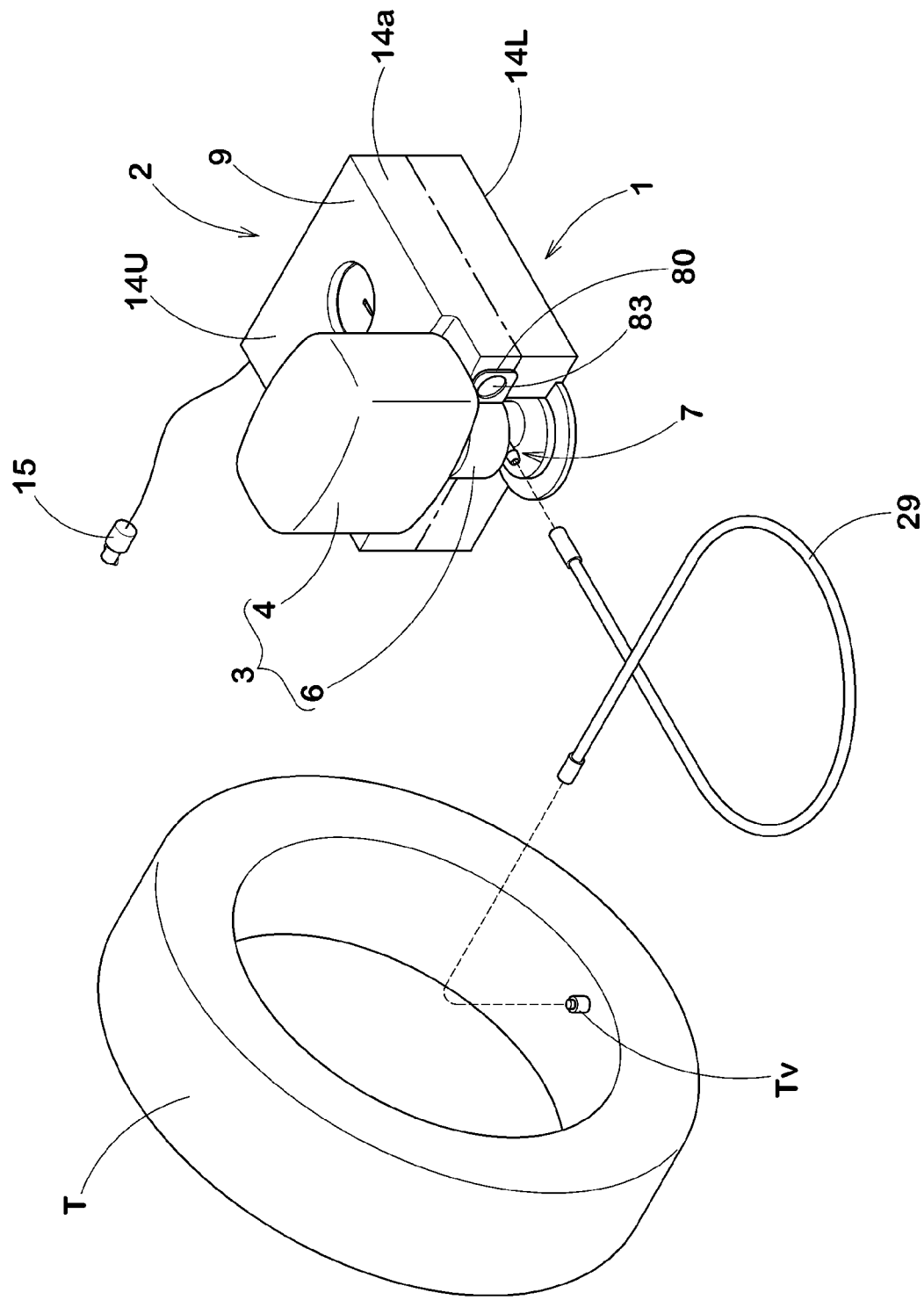
FIG. 1 A perspective view of the present invention using a puncture repair kit for repairing a puncture.

As shown in FIG. 1, the puncture repair kit 1 of the first embodiment comprises a compressor device 2 and a bottle unit 3. The bottle unit 3 comprises a bottle container 4 containing puncture sealing agent and a cap 6 attached to its opening 5 (shown in FIG. 8).

Figure 24:
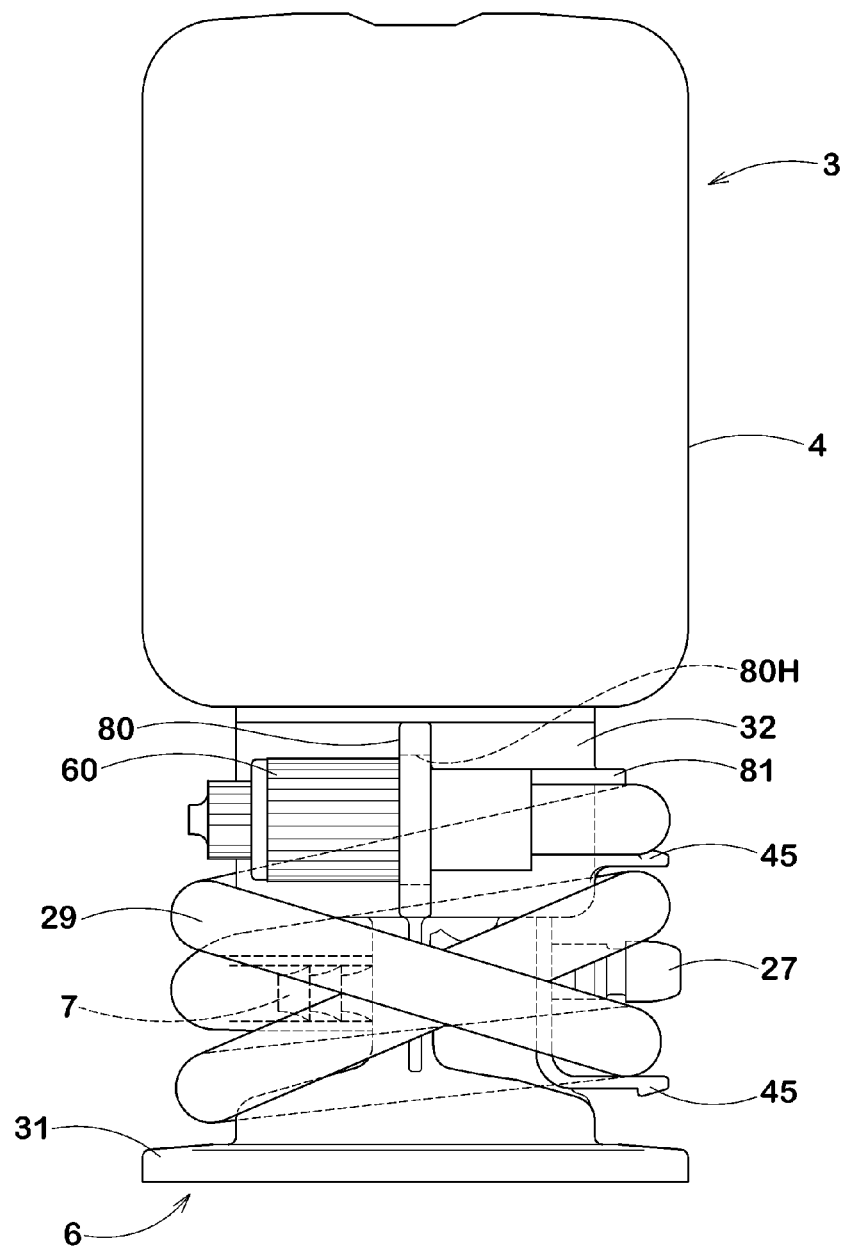
FIG. 24 A side view of the bottle unit showing a wrapping state of the feeding hose.

Thus, the above-mentioned compressor device 2 and the bottle unit 3 are directly connected without hose and the like intervention at a repairing scene of the represent puncture. Incidentally, a feeding hose 29 is previously connected to a sealing agent/compressed air removal port 7 disposed in the above-mentioned bottle unit 3. During storage in a car, this feeding hose 29 is stored while keeping the above-mentioned connecting state that the feeding hose is wrapped around the cap 6 as shown in FIGS. 24 and 25.

Figure 3:
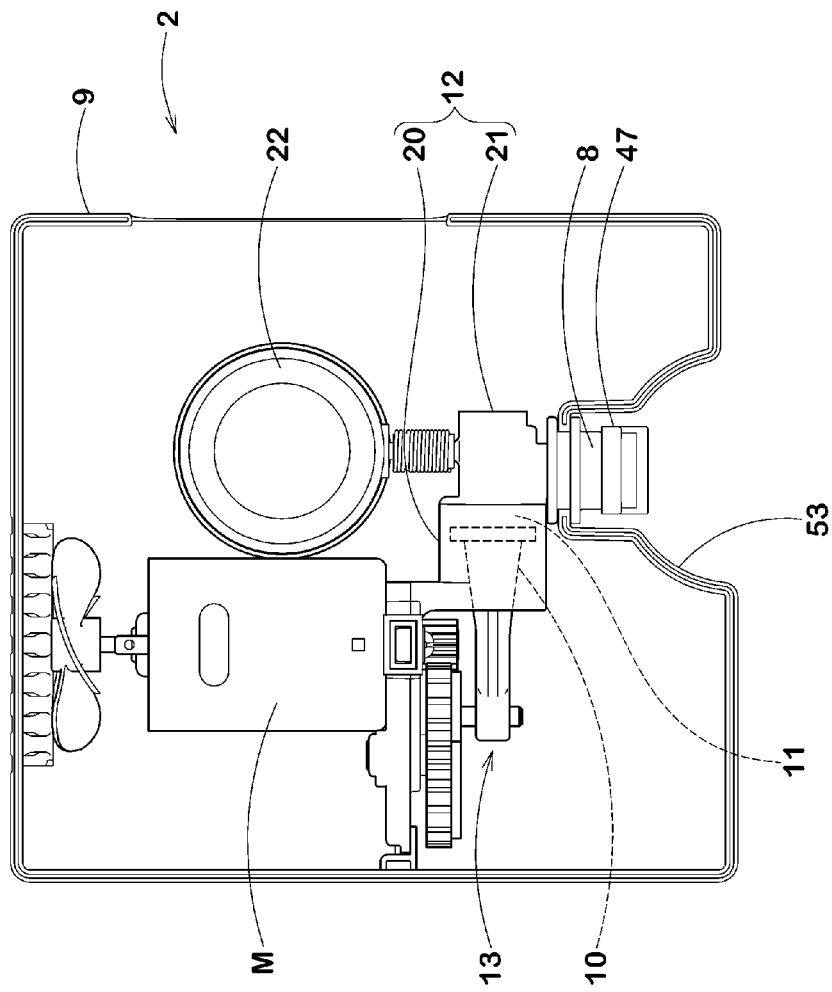
FIG. 3 A cross-sectional view showing its inside structure.

As shown in FIG. 3, the above-mentioned compressor device 2 contains a housing 9, at least a motor M and a compressor main body 13 comprising a cylinder 12 forming a pump chamber 11 between the motor and the piston 10 connected to the motor M.

Figure 2:
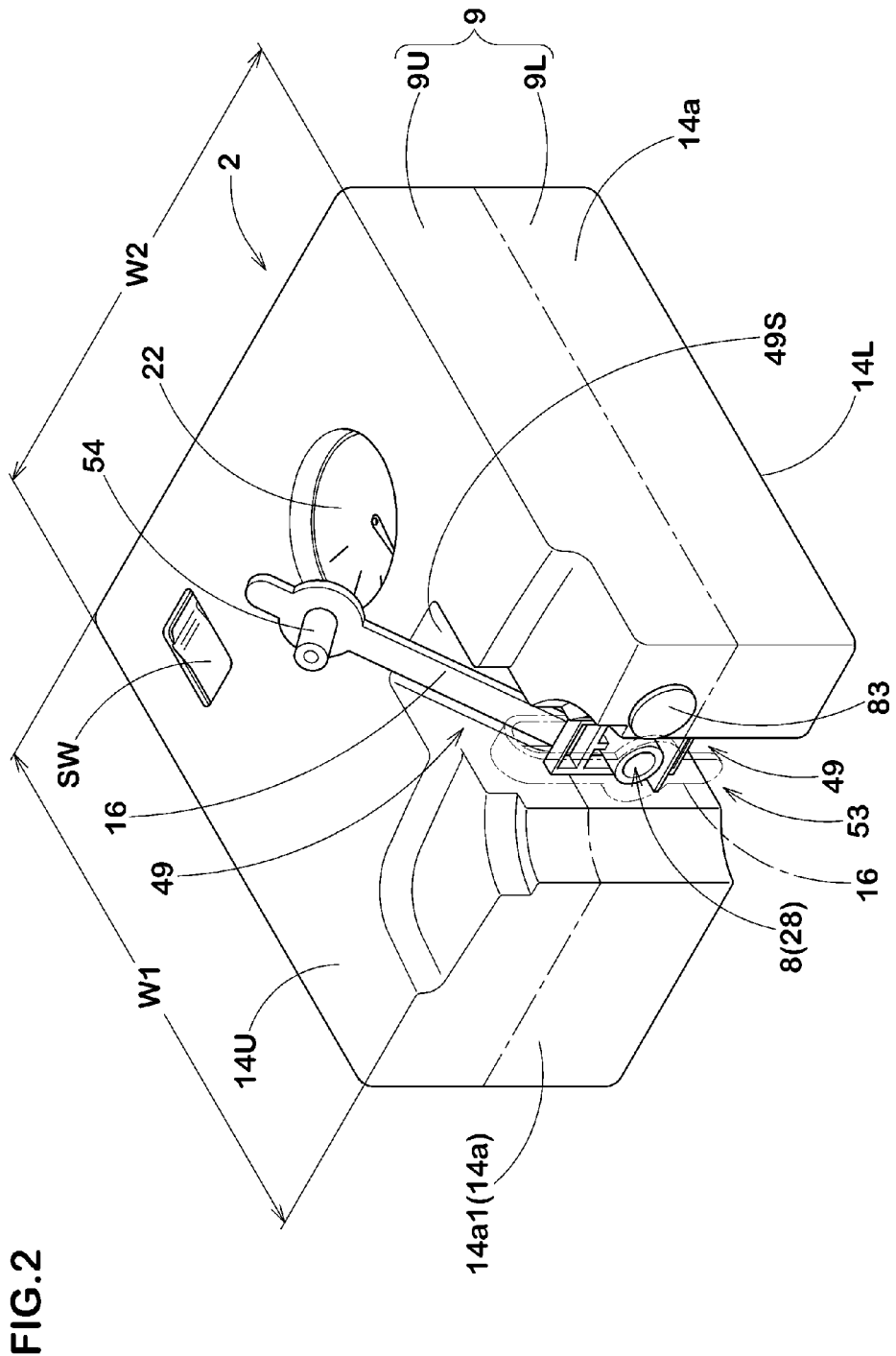
FIG. 2 A perspective view showing a compressor device.

As shown in FIGS. 1 and 2, the above-mentioned housing 9 is formed in a shape of a flat rectangular box with a low height, which has a peripheral wall having four sides surrounded by a side plate 14a, and an upper side plate 14U and a lower side plate 14L closing the upper end and lower end of the peripheral wall respectively. The housing 9 is formed with upper and lower case portions 9U and 9L which are decomposable.

For the above-mentioned motor M, a commercial-release various DC motor powered by an automobile 12 V direct current power supply can be used. To this motor M, a power-supply cord provided at its tip with a plug for power supply 15 which is connectable to an automobile cigar lighter socket is connected via an on-off switch SW attached to the upper side plate 14U of the above-mentioned housing 9. The plug for power supply 15 is contained in a recess (not shown) disposed in the above-mentioned lower side plate 14L so as to be freely removable.

Figure 4:
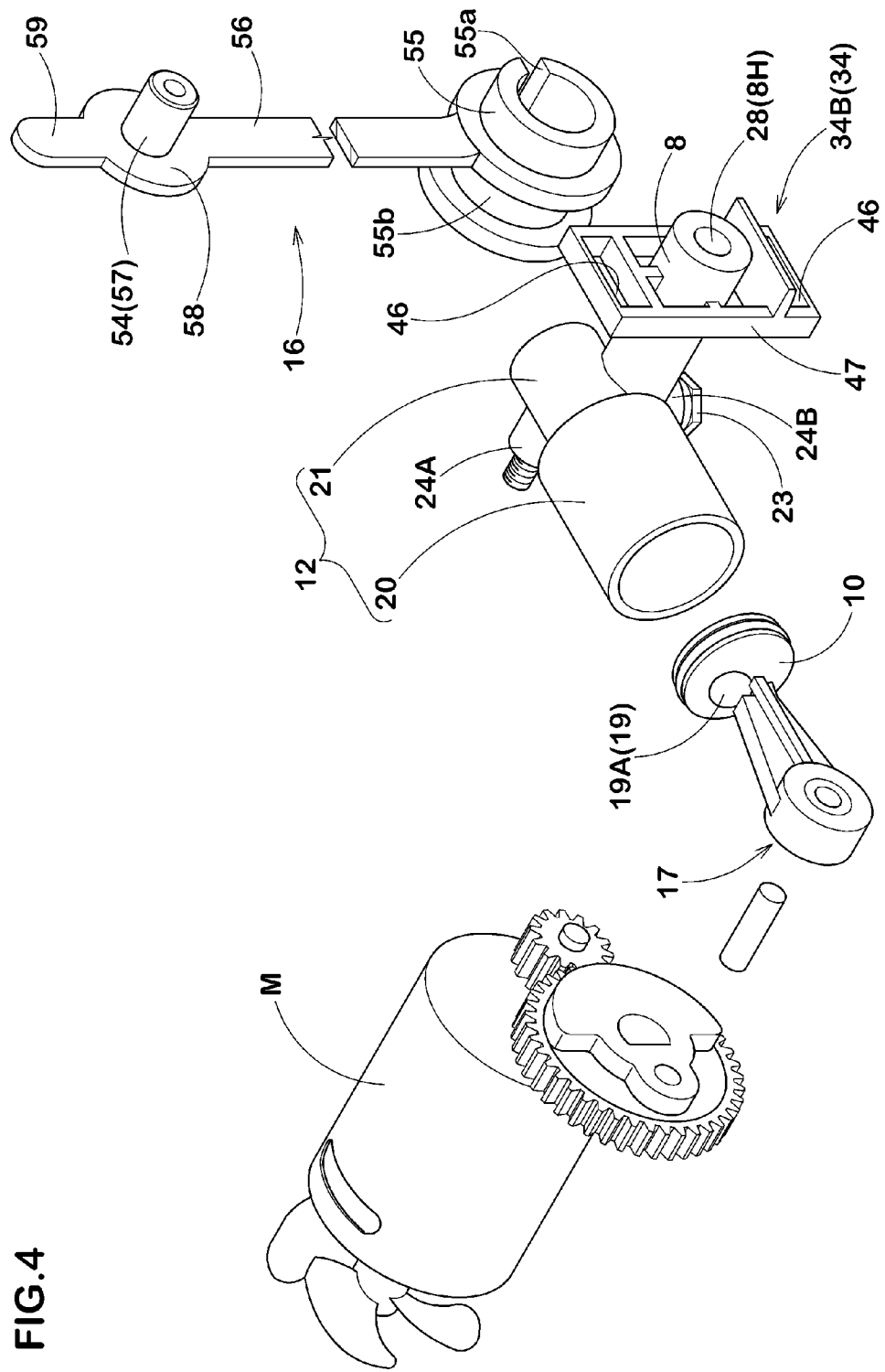
FIG. 4 A exploded perspective view showing a compressor main body.
Figure 5:
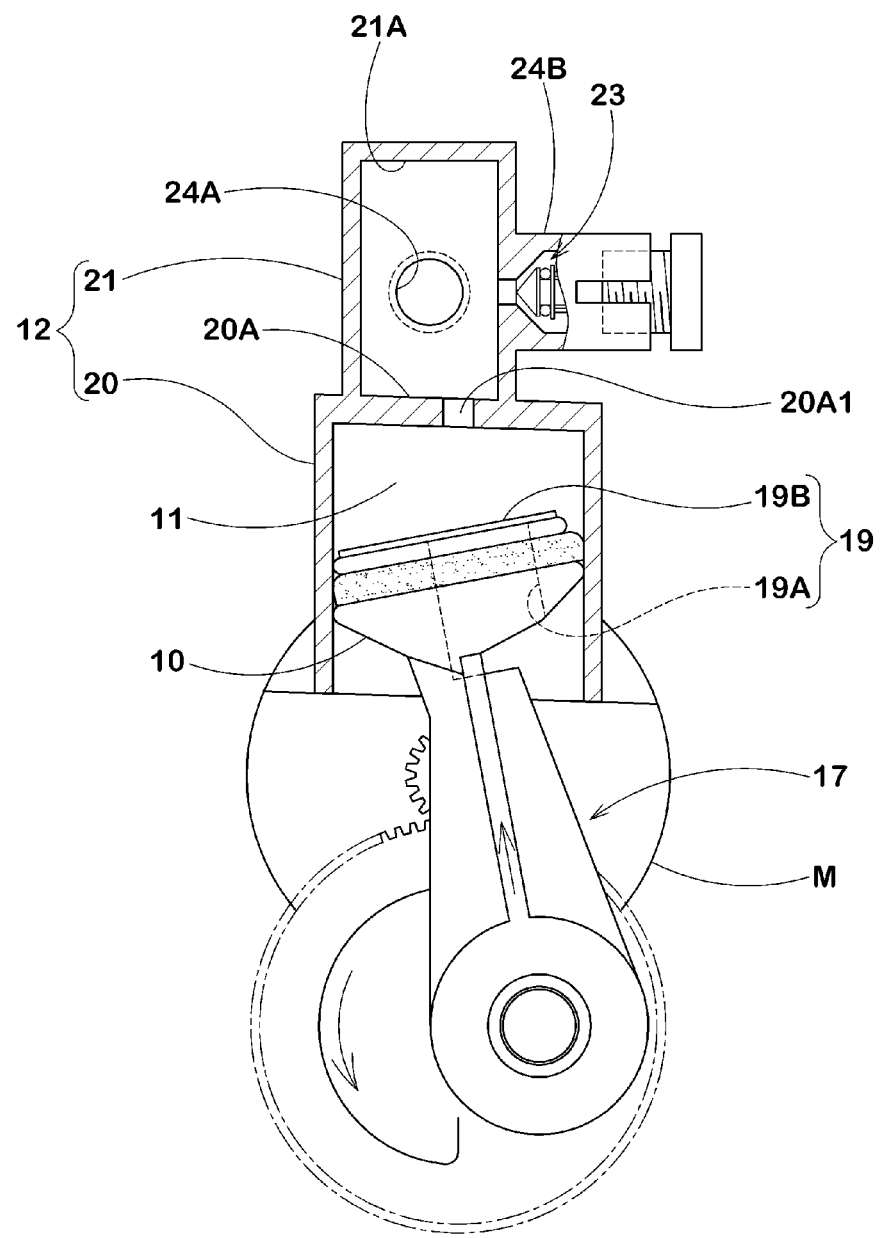
FIG. 5 A partial cross sectional view showing the main part thereof

The above-mentioned compressor main body 13 comprises, as shown in FIGS. 4 and 5, a piston 10 connected to the above-mentioned motor M via a crank mechanism 17, and a cylinder 12 enclosing reciprocatingly this piston 10 and forming a pump chamber 11 to compress the air between this cylinder and the piston 10. The piston 10 comprises an air intake valve 19 comprising an air intake hole 19A extending through this piston 10 in the direction of the shaft center, and a valve 19B closing this air intake hole 19A from the pump chamber side in spring property manner and formed of elastomer such as rubber, synthetic resin, metal and the like, for example.

In the present embodiment, the above-mentioned cylinder 12 is integrally provided with a cylinder subpart 21 to form a surge tank chamber 21A on a rear end side of the cylinder main body 20 forming the above-mentioned pump chamber 11 so as to retain the compressed air from the pump chamber 11 and reduce a dampen pulsation of pressure caused by the piston 10. In the present embodiment, the surge tank chamber 21A conducts to the pump chamber 11 via a small hole 20A1 formed in a partition wall 20A closing the rear end of the cylinder main body 20.

And in a peripheral wall of the above-mentioned cylinder subpart 21, a compressed air discharge port 8 is arranged in a protruding condition to discharge the compressed air. In the present embodiment, in the peripheral wall of the cylinder subpart 21, a first joining section 24A attached to a manometer 22 and a second joining section 24B attached to a relief valve 23 are provided in protruding conditions in a different orientation from each other.

Figure 6:
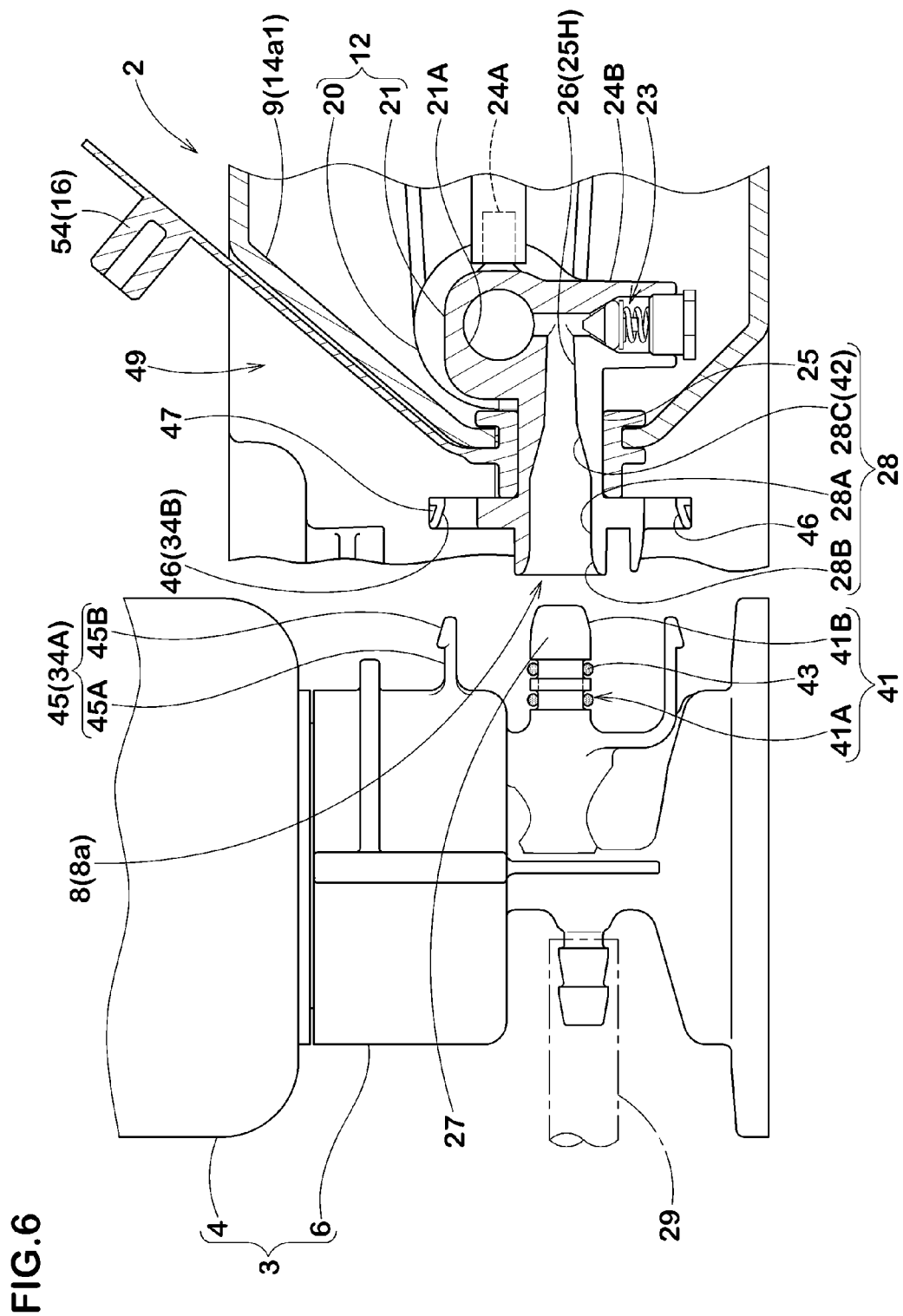
FIG. 6 A cross-sectional view showing a previous state of connecting between a compressed air discharge port and an air intake port.

As shown in FIG. 6, the above-mentioned compressed air discharge port 8 is provided with a cylindrical portion 25 protruding from the above-mentioned cylinder subpart 21 through the first side plate 14a1 and being provided on the tip side with an outlet port 8a to extrude the compressed air. A central hole 25H of this cylindrical portion 25 is provided with a discharge flow passage 26 extending from the above-mentioned surge tank chamber 21A to the outlet port 8a. And the central hole 25H is provided on an opening end side with a joint concave portion 28 connected to an air intake port 27 provided in the above-mentioned bottle unit 3. This joint concave portion 28 is continuously provided on the front and back of the parallel hole part 28A having a constant inside diameter with a forward and backward tapered surfaces 28B and 28C forming a tapered cone-shape toward the cylinder subpart 21.

The above-mentioned bottle unit 3 comprises the bottle container 4 containing the puncture sealing agent and the cap 6 attached to its opening 5. The bottle unit 3 is directly connected with the above-mentioned compressor device 2 in the inverted state that the cap 6 is positioned downward.

Figure 8:
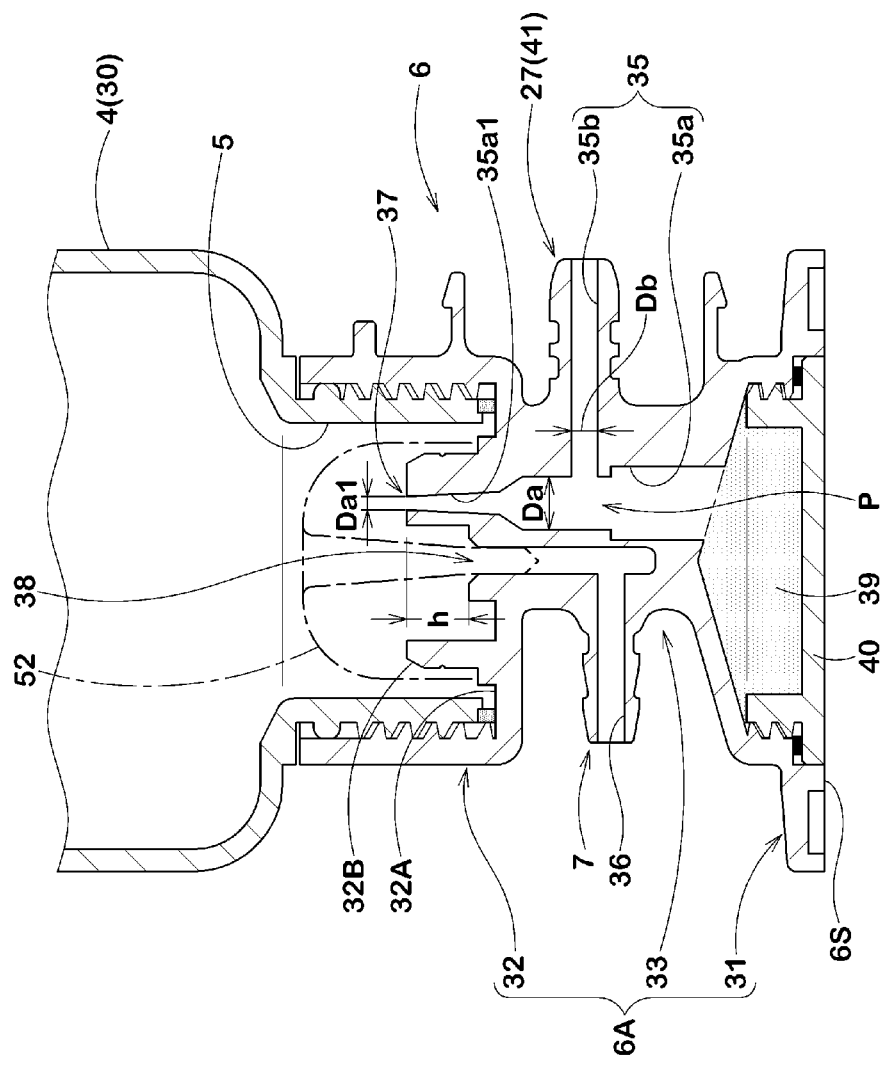
FIG. 8 A cross-sectional view showing a cap with the bottle container.
Figure 14:
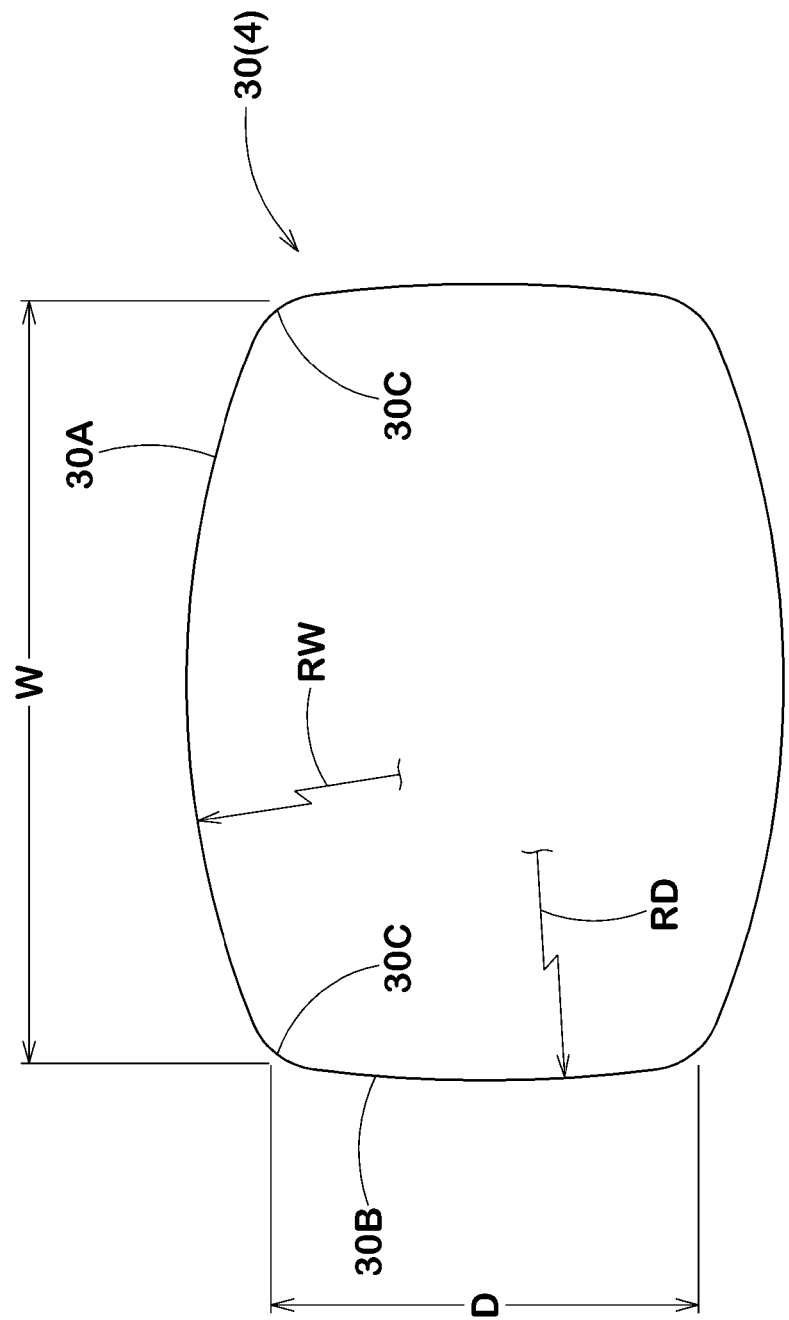
FIG. 14 A side cross-sectional view of a bottle trunk portion.

In the above-mentioned bottle container 4, as shown in FIG. 8, the small-diameter cylindrical opening 5 protrudes at a lower end of the bottle trunk portion 30 to move the puncture sealing agent in and out. In the present embodiment, as shown in FIG. 14, a cross-section perpendicular to the height direction of the bottle trunk portion 30 is formed as a substantially rectangle surrounding the four sides with a pair of long side parts 30A convexing in arc-like fashion toward an outside of the bottle, and a pair of short side parts 30B concaving in arc-like fashion.

Thus, when
  a length of the long side part 30A is defined as W,
  a radius of curvature of the long side part 30A is defined as RW,
  a length of the short side part 30B is defined as D, and
  a radius of curvature of the short side part 30B is defined as RD in the present embodiment, they meet the following relations (1) to (3):

$$1.3 \leq W/D \leq 1.7 \tag{1}$$

$$0.5 \leq RW/W \leq 3.0 \tag{2}$$

$$0.5 \leq RD/D \leq 20.0 \tag{3}$$

In view of the storage behavior of the puncture repair kit 1 in the car, more particularly in a trunk of the car for example, the above-mentioned compressor device 2 is substantially cuboid so that the bottle trunk portion 30 of the bottle container 4 is preferably formed in substantially cuboid shape. However, a high inner pressure of nearly 350 kPa, for example, exerts through the bottle container 4 at a time of puncture repairing. At this time, in the case that the bottle trunk portion 30 has a round cross-sectional, the bottle trunk portion 30 is inflated evenly in the radial direction by an internal pressure. Therefore, a deformation at a time of compressing air filling is not aware, which causes a user less uneasiness. However, in the bottle case that the trunk portion 30 is a rectangle cross-sectional, the inflation caused by the internal pressure is not even, and it is inflated from a rectangle cross-sectional shape to a round cross-sectional shape. Then, the user would feel that its deformation amount is much greater than in reality. Therefore, even if it is within the range of pressure resistance, there is a possibility to cause the user uneasiness of burst and the like.

In the present embodiment, the above-mentioned long side part 30A and the short side part 30B are formed as convex arc shapes respectively so as to have a nearly deformed shape at the time of inflated state. Therefore, it is possible that the deformation at the time of inflated state is not really felt by the user while improving the storage behavior and decreasing the uneasiness feeling of the user.

Accordingly, it is important to inhibit a volume of inflating on a longer side in order to avoid the above-mentioned uneasiness. To achieve this, the long side length W is preferably set to be large, and the radius of curvature RW is preferably set to be small. When the ratio W/D is less than 1.3, or when the ratio RW/W is over 3.0, the above-mentioned length W relatively becomes small, or an increase of inflation volume of the long side length occurs since the radius of curvature RW becomes large. When the above-mentioned ratio W/D is over 1.7, or when the ratio RW/W is less than 0.5, the storage behavior becomes deteriorated. And, when the ratio RD/D is over 20.0, the inflation volume of the short side length increases, and the deformation at the time of compressing air filling becomes large. However, when the ratio RD/D is less than 0.5, the storage behavior deteriorates. Based on this standpoint, the lower limit of the ratio W/D is preferably not less than 1.4, and the upper limit is preferably not more than 1.6. The lower limit of the ratio RW/W is preferably not less than 0.7, and the upper limit is preferably not more than 2.0. The lower limit of the radio RD/D is preferably not less than 1.0, and the upper limit thereof is preferably not more than 10.0.

Incidentally, to reduce the stress concentration and to improve the pressure resistance, it is preferable to form a corner portion where the long side part 30A and the short side part 30B intersect as an arc 30C having a radius of curvature of 15 mm±5 mm.

Figure 9:
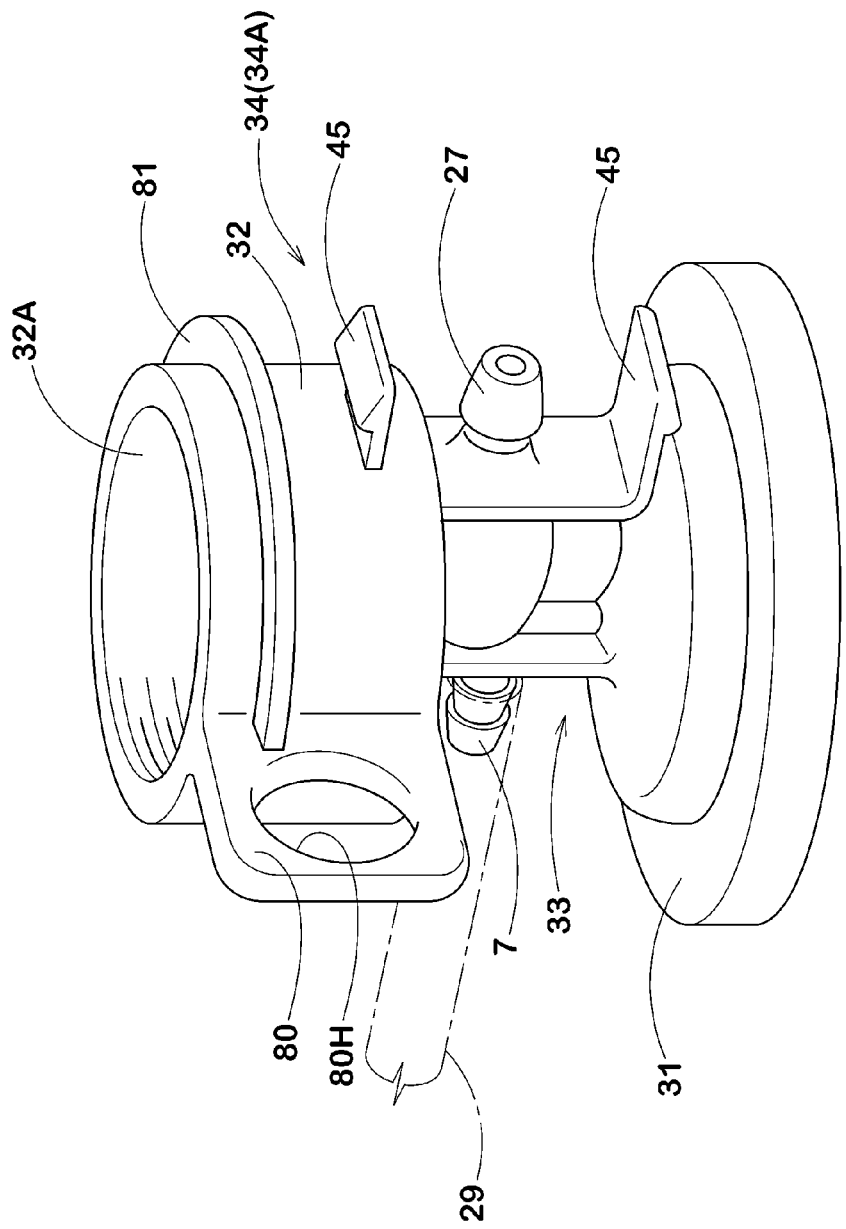
FIG. 9 A perspective view showing an exterior appearance of the cap.
Figure 10:
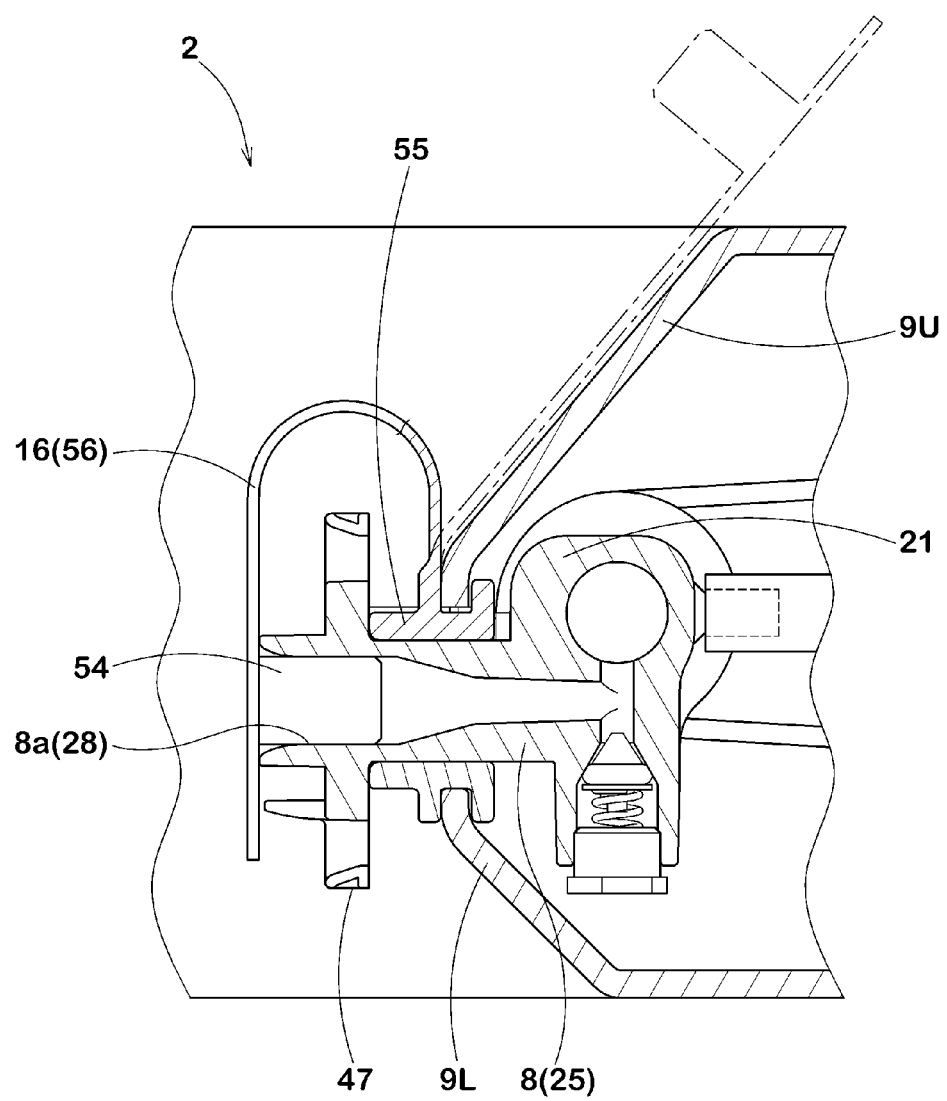
FIG. 10 A cross-sectional view of a dust-proof cap showing an attaching state to the compressed air discharge port.
Figure 11:
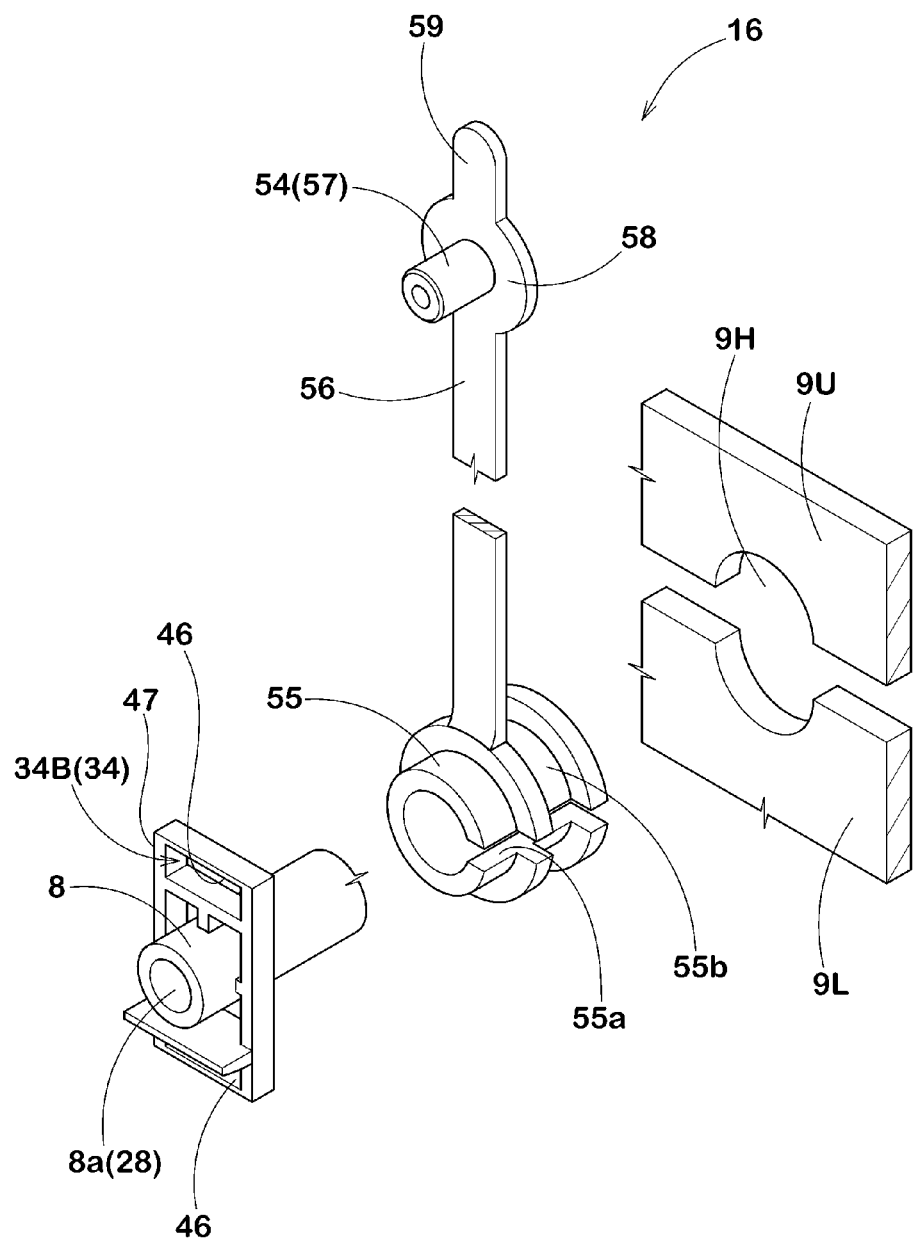
FIG. 11 A perspective view of the dust-proof cap.
Figure 12:
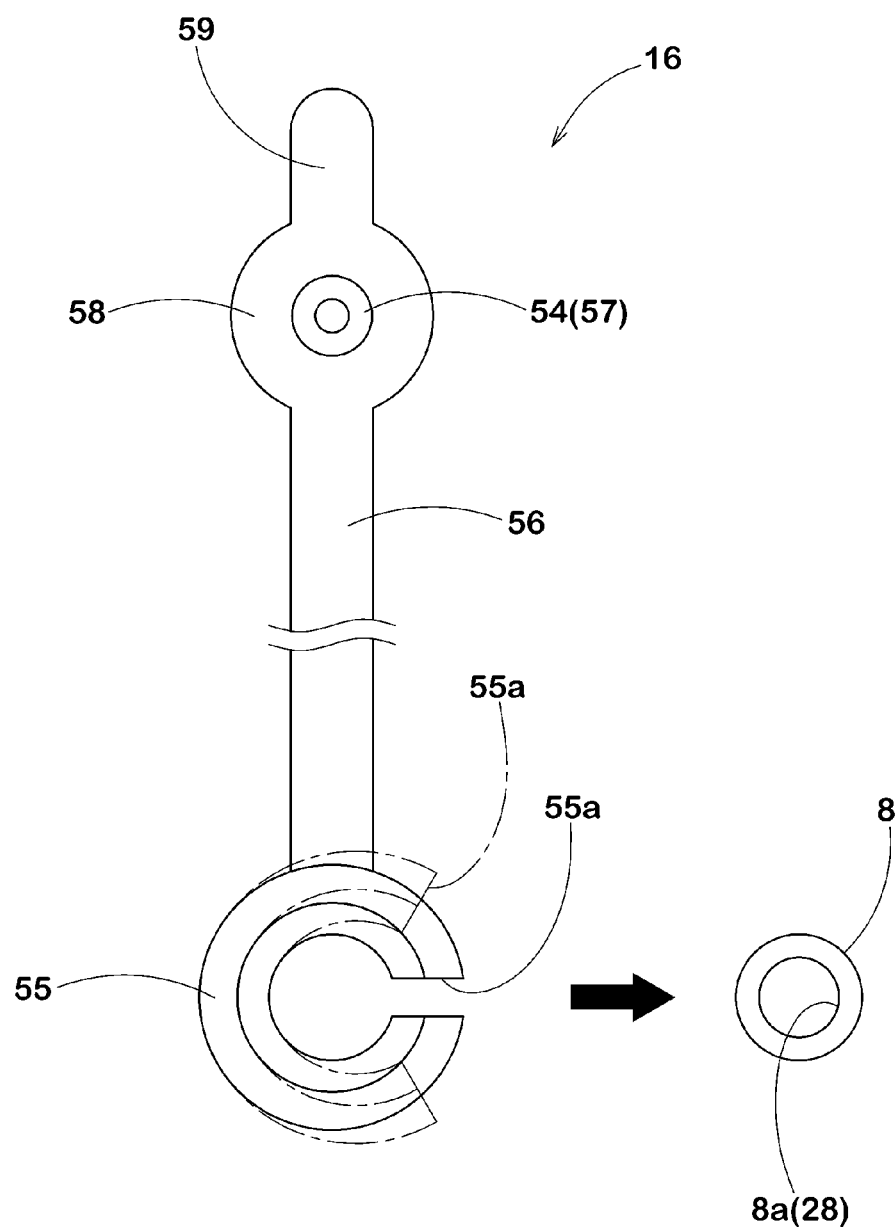
FIG. 12 A front view of the dust-proof cap.

As shown in FIGS. 8 and 9, the above-mentioned cap 6 comprises the air intake port 27 sending the compressed air from the above-mentioned compressed air discharge port 8 into the bottle container 4, and the sealing agent/compressed air removal port 7 to bring out in succession the puncture sealing agent and the compressed air from the bottle container 4 by sending this compressed air.

More particularly, the above-mentioned cap 6 comprises a cap main portion 6A comprising integrally a discoid basal plate 31 forming a basal plane 6S, a bottle attaching part 32 to attach the opening 5 of the above-mentioned bottle container 4, and a waist part 33 disposed therebetween. And, in this cap main portion 6A, formed are an extending air flow passage 35 extending from the above-mentioned air intake port 27 into the opening 5 of the bottle container 4, and a sealing agent/compressed air removal flow passage 36 extending from the sealing agent/compressed air removal port 7 into the opening 5 of the bottle container 4.

The above-mentioned bottle attaching part 32 comprises an attaching concave part 32A to fix the above-mentioned opening 5, and a boss portion 32B rising from a basal plane of this attaching concave part 32A. The attaching concave part 32A is capable of helically attaching the opening 5 provided in its sidewall face with an inside screw. And, a top surface of the above-mentioned boss portion 32B is provided with an air flow passage upper opening 37 where a top end of the above-mentioned air flow passage 35 opens, and with a sealing agent/compressed air removal flow passage upper opening 38 where a top end of the sealing agent/compressed air removal flow passage 36 opens.

The above-mentioned air flow passage 35 comprises a vertical air flow passage 35a extending inferiorly from the above-mentioned air flow passage upper opening 37 and a horizontal air flow passage 35b intersecting with this vertical air flow passage 35a at right angle at an intersection point P and extending from the intersection point P to the air intake port 27. In a lower end part beyond inferiorly the intersection point P of the vertical air flow passage 35a, in case the puncture sealing agent flows backward from the air flow passage upper opening 37, there is a sealing agent container 39 for taking in the flowing backward puncture sealing agent. The sealing agent container 39 has a larger diameter than the vertical air flow passage 35a.

In the puncture repairing, the user first of all infuses a punctured tire T with the puncture sealing agent and compressed air in succession by use of the puncture repair kit 1 and pumps up the tire. Then, the user takes once the puncture repair kit 1, which is disengaged from the tire T and in which the compressor device 2 and the bottle unit 3 have been connected, onto his/her car and runs the car during about ten minutes in order to seal the puncture hole. Finally, the puncture repair kit 1 is connected again to the tire T to check and to refill the air pressure. This will complete the puncture repairing. In this puncture repairing process, the bottle unit 3, after sealing agents are filled up, leans toward various directions and is vibrated. It is possible that the puncture sealing agent remaining in this bottle unit 3 flows backward from the air flow passage upper opening 37 to the compressor device 2, and that the compressor device 2 would be damaged.

Then, in this example, as mentioned above, the air flow passage 35 comprises the vertical air flow passage 35a and the horizontal air flow passage 35b intersecting with this vertical air flow passage at the right angle at the intersection point P. In a lower end part of the vertical air flow passage 35a, there is a sealing agent container 39. Therefore, when the puncture sealing agent flows backward from the air flow passage upper opening 37 into the vertical air flow passage 35a, the puncture sealing agent can flow into and be contained in the lower end of the sealing agent container 39 without divaricating into the horizontal air flow passage at the intersection point P.

Incidentally, an adequate content of the sealing agent container 39 is about the same quantity of sealing agent remaining inside the bottle unit 3; that is, it ranges between 5 and 15 cc. Incidentally, when the content is less than 5 cc in the present embodiment, it is possible to fail to contain the flown backward sealing agent. The quantity of over 15 cc goes to waste, and this causes the cap 6 to grow in size unnecessarily, which would deteriorate the storage behavior.

To prevent the above-mentioned flowing backward from the air flow passage upper opening 37, it is preferable that the above-mentioned vertical air flow passage 35a is provided on its upper end side with a squeezing part 35a1 for reducing the inside diameter so as to reduce an inside diameter Da1 of the air flow passage upper opening 37 into a range between 1.0 and 2.0 mm. At the position of the above-mentioned intersection point P, an inside diameter Da of the vertical air flow passage 35a is set to be larger than an inside diameter Db of the horizontal air flow passage 35b; and this improves a suppressive effect of flowing from the vertical air flow passage 35a into the horizontal air flow passage 35b. In the present embodiment, the inside diameter Db of the horizontal air flow passage 35b is about from 3.0 to 5.0 mm. It is also preferable to open this air flow passage upper opening 37 above the sealing agent/compressed air removal flow passage upper opening 38 in order to inhibit the flowing backward from the air flow passage upper opening 37; and in particular, a height (h) of the air flow passage upper opening 37 measured from the sealing agent/compressed air removal flow passage upper opening 38 is preferably in a range of from 5.0 to 7.0 mm.

The above-mentioned sealing agent container 39 opens in the basal plane 6S of the above-mentioned cap 6, and this opening is closed by a container portion cover 40 being flush with the basal plane 6S.

The above-mentioned air intake port 27 comprises a connecting nozzle 41 protruding from the above-mentioned waist part 33 toward the above-mentioned compressed air discharge port 8. Thus, since this connecting nozzle 41 engages with the above-mentioned joint concave portion 28, the compressed air discharge port 8 and the air intake port 27 can be directly connected.

Figure 7:
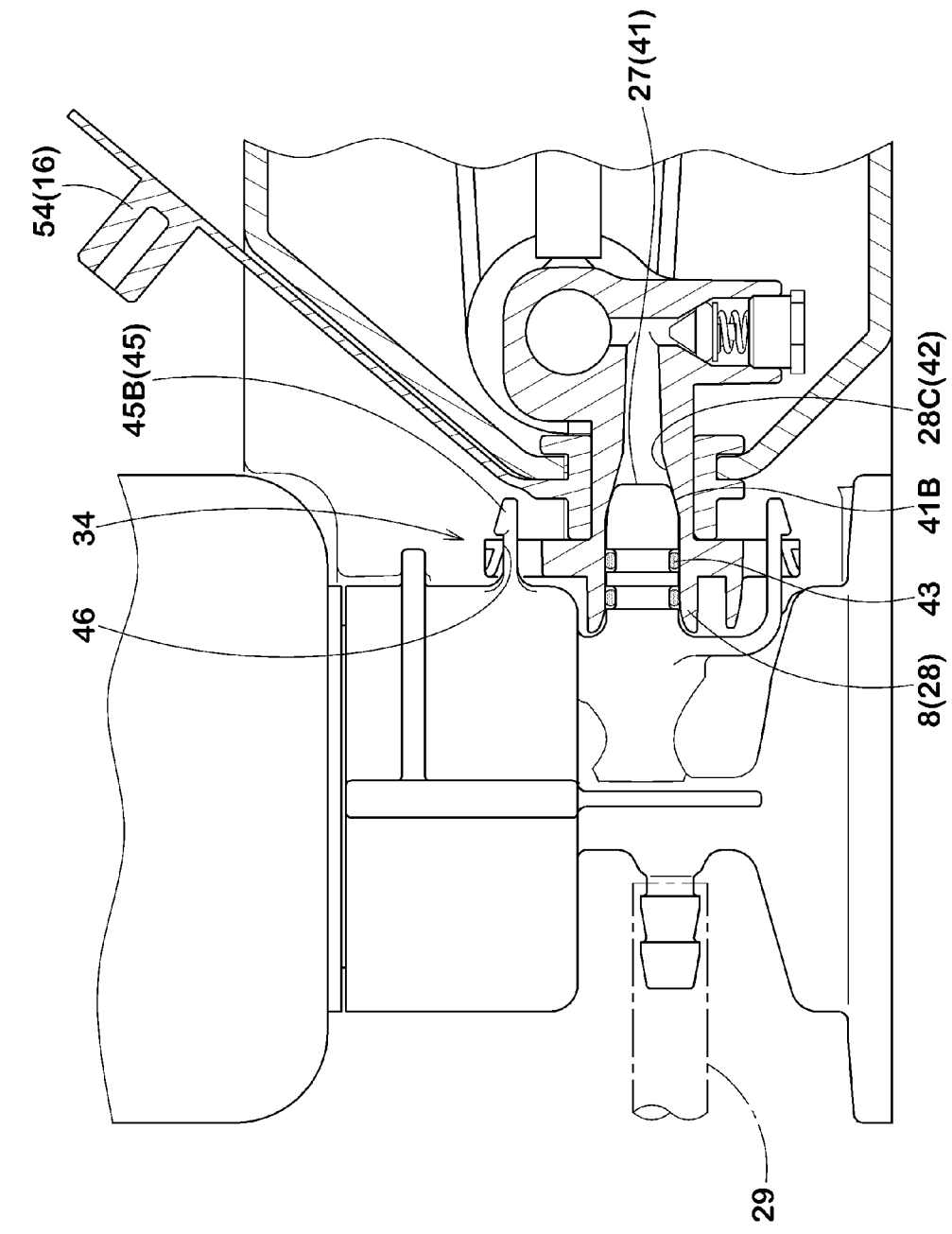
FIG. 7 A cross-sectional view showing the state of connecting between the compressed air discharge port and the air intake port.

As shown in FIGS. 6 and 7, the above-mentioned connecting nozzle 41 is provided with a tapered surface 41B having a tapered cone shape on a tip end side of the nozzle main body 41A having a constant outer diameter. This tapered surface 41B is inclined as substantially same as the rear tapered surface 28C of the above-mentioned joint concave portion 28. Therefore, the rear tapered surface 28C forms a nozzle receiving surface portion 42 abutting on the tapered surface 41B and receiving the tapered surface 41B when letting the connecting nozzle 41 into the joint concave portion 28. This will allow the connecting nozzle 41 to connect directly with the joint concave portion 28 at a concentrical and exact position. Incidentally, the front tapered surface 28B of the joint concave portion 28 works as a guide to receive the connecting nozzle 41.

The above-mentioned connecting nozzle 41 is provided around the above-mentioned nozzle main body 41A with an O-shaped ring 43 sealing between the connecting nozzle and an inner surface of the above-mentioned joint concave portion 28 (in the present embodiment, an inner surface of the parallel hole part 28A). In the present embodiment, two of the O-shaped rings 43 for ensuring sealing are arranged as an example. The O-shaped rings 43, consumable supplies, are arranged on the bottle unit 3; this helps to use the compressor device 2 repeatedly without maintenance.

The puncture repair kit 1 according to the present embodiment is provided with a securing device 34 to prevent defacement of its environment by the puncture sealing agent because of disconnection between the above-mentioned compressed air discharge port 8 and the air intake port 27 under repairing the punctured tire.

This securing device 34 comprises a locking device 34A disposed in the above-mentioned cap 6 and an interlocking device 34B formed in the above-mentioned compressor device 2. In the present embodiment, the above-mentioned locking device 34A comprises, a pair of locking click 45 protruding on the both (in the present embodiment, upper and lower) sides of the connecting nozzle 41 of the above-mentioned air intake port 27 toward the compressor device 2. In the present embodiment, the interlocking device 34B is made of a click interlocking hole 46 disposed at a position facing the locking click 45 and being capable of preventing from falling-off by interlocking with the locking click 45.

The above-mentioned locking click 45 is provided at a tip of the main part 45A, extending in parallel to the connecting nozzle 41 from the above-mentioned cap main portion 6A, with a hooking part 45B having a rectangular triangle shape. Thus, the above-mentioned click interlocking hole 46 interlocks with the hooking part 45B and is formed as a rectangle hole in this example.

The locking click 45 and the cap main portion 6A are formed as an integrally formed body comprising plastic such as nylon, polypropylene, polyethylene and the like, for example, or reinforced plastic containing those and short fiber such as fiberglass and the like. In the present embodiment, the above-mentioned click interlocking hole 46 comprises, a frame 47 supported by the above-mentioned cylindrical portion 25 forming the above-mentioned joint concave portion 28. This frame 47, the cylindrical portion 25, and the cylinder 12 are formed as an integrally formed body made of light weight alloy such as zinc alloy, aluminum alloy and the like, for example. Therefore, necessary strength can be assured.

Figure 15:
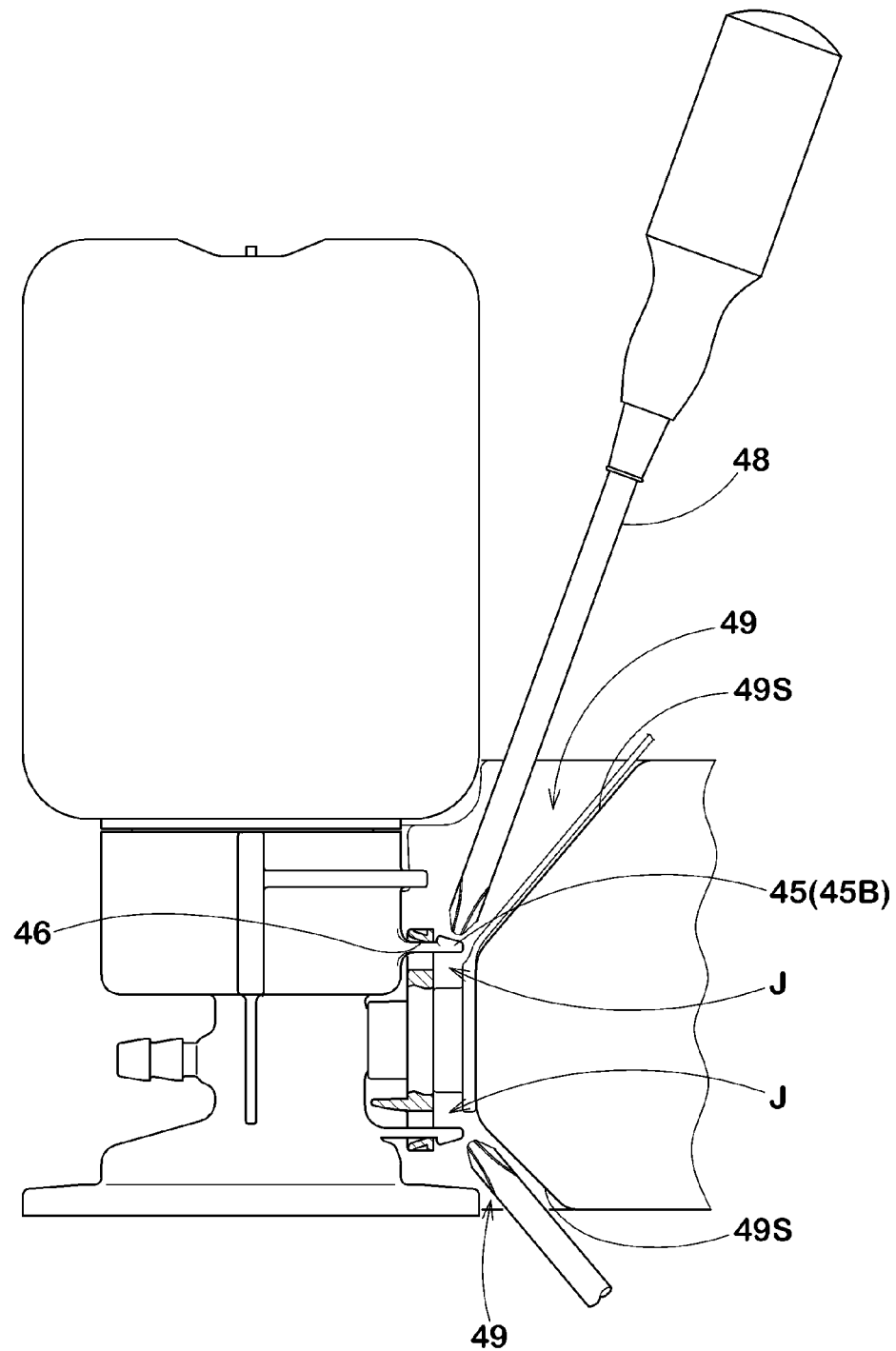
FIG. 15 A cross-sectional view showing a guide groove and its function.

In the present embodiment, as shown in FIGS. 2 and 15, the above-mentioned compressor device 2 is provided in the above-mentioned housing 9 with a guide groove 49 for leading a rod-like jig 48 such as a screw driver, for example, into an interlocking part J between the above-mentioned locking click 45 and the click interlocking hole 46 so as to release the interlocking. This guide groove 49 is an inclined groove having a groove basement 49S inclined toward the interlocking part J as a guide surface. The guide groove 49 can lead the rod-like jig 48 into interlocking part J between the groove basement 49S and the groove-sidewall faces on its both sides. The above-mentioned locking click 45 comprises outwardly the above-mentioned hooking part 45B, and the above-mentioned interlocking can be easily released with pushing inwardly the hooking part 45B by the rod-like jig 48.

Owing to the pushing of the compressor device 2 of the bottle unit 3, a direct connection between the above-mentioned compressed air discharge port 8 (in the present embodiment, joint concave portion 28) and the air intake port 27 (in the present embodiment, connecting nozzle 41), and an interlocking between the above-mentioned locking click 45 and the click interlocking hole 46 are simultaneously achieved. At this time, the pushing power is preferably in a range between 3 and 6 kgf. When the pushing power is over 6 kgf, the operability will enormously decrease; and when it is less than 3 kgf, the fixation will be weak, and it may cause a disconnection owing to the internal pressure at a time of inflating the tire.

Consequently, in the puncture repair kit 1 according to the present embodiment, the compressor device 2 and the bottle unit 3 are directly connected without any hoses intervention. Therefore, the bottle unit 3 can become integral with the compressor device 2 so as to lower the center of gravity point, and the stability can be improved. Moreover, the bottle unit 3 becomes not to be connected with the air supply hose from the compressor device 2, and not to be pushed by the air supply hose; and the bottle falling can be effectively prevented. At this time, in the above-mentioned directly connecting state, it is important that the basal plane 6S of the above-mentioned cap 6 and the basal plane 2S of the compressor device 2 are flush with each other. This makes the ground contacting area increased, and it can increase the friction force of the road surface at the compressor operating time, it can improve not only the installation stability but also the vibration stability at the time of the compressor vibrating.

In the present embodiment, owing to the above-mentioned securing device 34, the bottle unit 3 and the compressor device 2 can be fixed with just a single operation at the same time of the above-mentioned direct connection, which helps to prevent a lose of the connection at the time of puncture repairing and to increase the safety.

Figure 16:
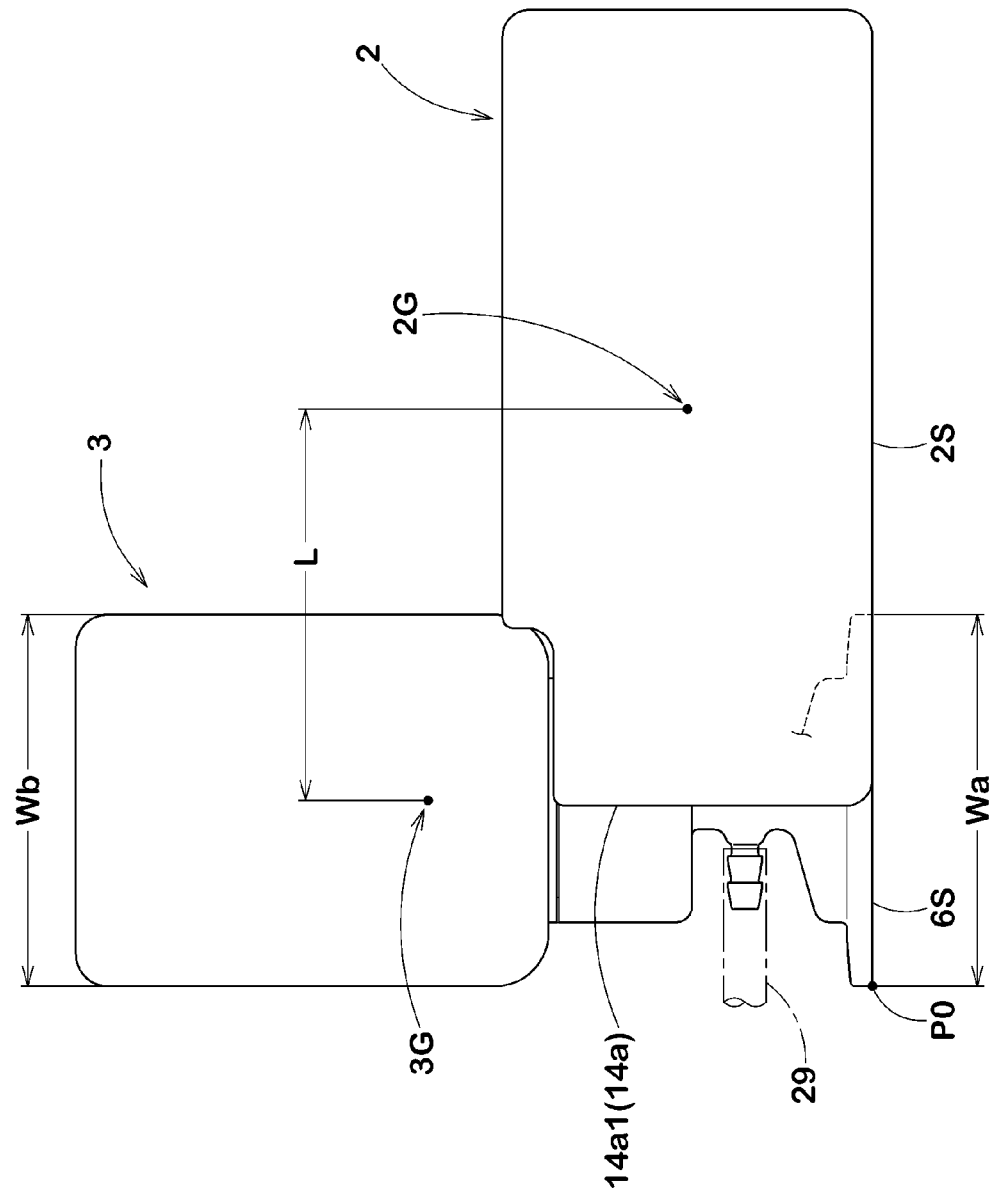
FIG. 16 A side view of a connected state of the compressor device and the bottle unit.

The above-mentioned bottle unit 3 is directly connected on the first side surface of the compressor device 2, in the present embodiment, on the above-mentioned side plate 14a1. As shown in FIG. 16, a width Wa of the basal plane 6S of the above-mentioned cap 6 at right angle to the first side surface (in the present embodiment, side plate 14a1) is preferably substantially equivalent to the width Wb of the above-mentioned bottle container 4 in right angle direction. In viewpoint of the storage behavior, the width Wa is preferably not more than the width Wb. In contrast, a pivot point PO of a falling of the puncture repair kit 1 is equal to an outer edge of the basal plane 6S of the cap 6 in the right angle direction. Therefore, the more outside this pivot point PO at the above-mentioned right angle is located, the more the falling moment is improved, and the less the puncture repair kit becomes falling down. Therefore, when the width Wa and the width Wb are set to be substantially the same, it becomes possible not to undermine the storage behavior but to improve the fall-prevention efficacy.

As shown in FIG. 2, when the compressor device 2 has a rectangle shape of which a first width W1 is longer than a second width W2, it is preferable to connect the above-mentioned bottle unit 3 on the shorter side plate 14a1. Therefore, as shown in FIG. 16, this can increase a distance L between the center of gravity point 2G of the compressor device 2 and the center of gravity point 3G of the bottle unit 3, and the fall moment increases; therefore, the puncture repair kit becomes less falling down.

The above-mentioned first side surface (in the present embodiment, side plate 14a1) of the compressor device 2 is provided with a substantially semicircle concave portion 53 that fits an outer surface shape of the above-mentioned bottle unit 3 and stabilizes the seating of the bottle unit 3.

Figure 17A:
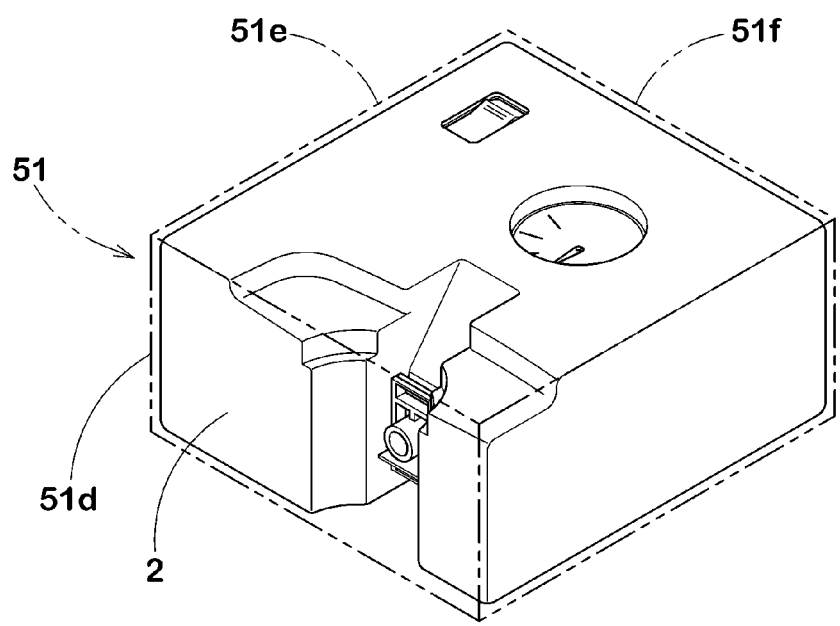
FIGS. 17 (A) and (B): Perspective views showing a circumscribed cuboid of the compressor device and the bottle unit.
Figure 17B:
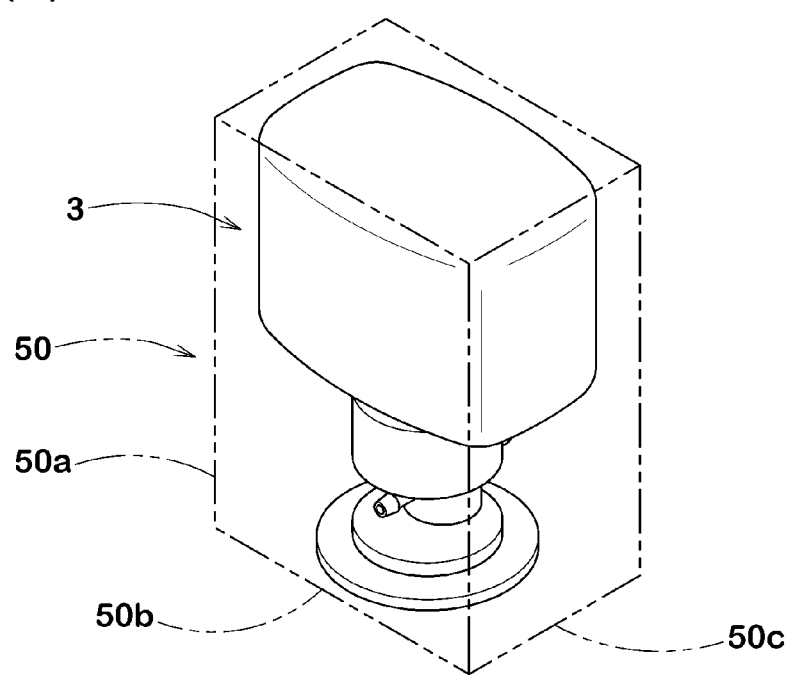

In view of storage behavior, as shown in FIGS. 17(A) and 17(B), in the above-mentioned bottle unit 3, lengths of two sides among three sides 50a, 50b, and 50c of the bottle-side circumscribed cuboid 50 circumscribed by the surface of this bottle unit 3 and lengths of two sides among three sides 51d, 51e, and 51f of the compressor-side circumscribed cuboid 51 circumscribed by the surface of the above-mentioned compressor device 2 are preferably of equal length.

Figure 18A:
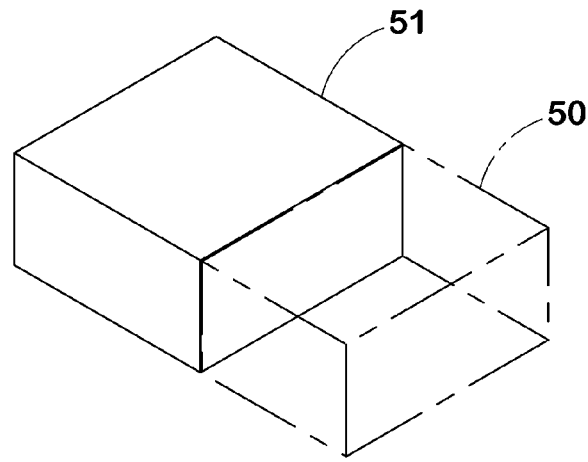
FIGS. 18 (A) to (C): Perspective views explaining their functions.
Figure 18B:
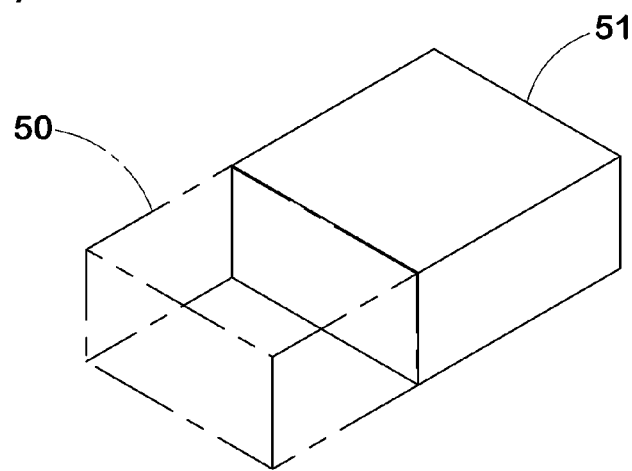
Figure 18C:
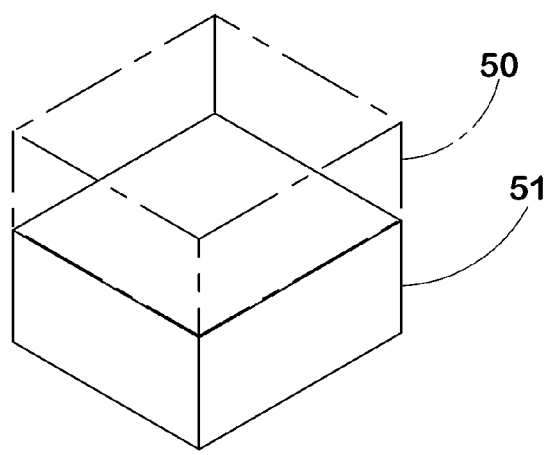

As shown in FIGS. 18(A) to 18(C), the bottle-side circumscribed cuboid 50 and the compressor-side circumscribed cuboid 51 can be stacked on one another without unevenness so as to cut waste of storage space and to improve the storage behavior in the car.

As shown in FIGS. 2 and 10 to 12, the above-mentioned compressor device 2 is provided with a dust-proof cap 16 to prevent an entry of a foreign substance into the above-mentioned joint concave portion 28 during storage.

This dust-proof cap 16 comprises a cap portion 54 capable of being attached to and removed from the outlet port 8a of the above-mentioned cylindrical portion 25 and of covering the above-mentioned outlet port 8a owing to the attachment; and a ring securing part 55 outserted in the above-mentioned cylindrical portion 25, and a bendable joining section 56 connecting between the above-mentioned cap portion 54 and the ring securing part 55.

In the present embodiment, the cap portion 54 is formed of a stop 57 capable of being inserted into the outlet port 8a as an example. The incidentally cap portion 54 comprises a stopper part 58 having a larger diameter than the outlet port 8a, limiting an insert depth of the stop 57 into the outlet port 8a, and a tip-like knob part 59 making easy to take it off from the outlet port 8a.

The above-mentioned ring securing part 55 is outserted between the above-mentioned cylinder subpart 21 and the frame 47 into the above-mentioned cylindrical portion 25. This ring securing part 55 has a C-shaped form in a cross-section, which has a slit 55a on its side part. The cylindrical portion 25 can be attached and removed through the slit 55a. The above-mentioned joining section 56 is bendable belt-like; in the present embodiment, the above-mentioned dust-proof cap 16 is formed as an integrally formed body in which the cap portion 54, the ring securing part 55, and the joining section 56 are integrally made of synthetic resin.

Around the outer circumference of the ring securing part 55, there is a circumferential-groove-like retention groove 55b to retain an inner peripheral edge of a through-hole 9H of the above-mentioned housing 9 through which the above-mentioned cylindrical portion 25 passes. This retention groove 55b is formed more inside (on the cylinder subpart 21) than the above-mentioned joining section 56.

Figure 13:
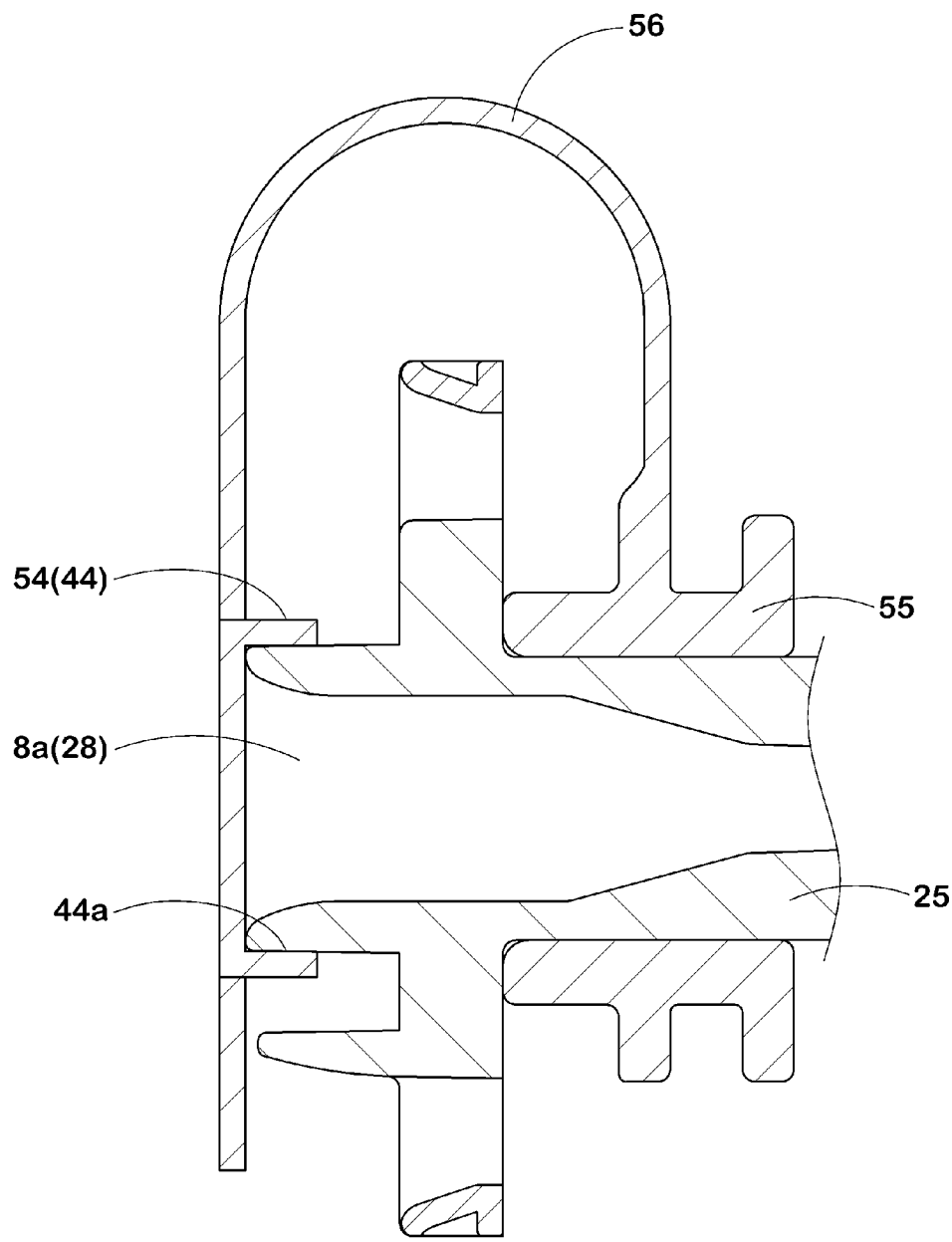
FIG. 13 An exhibit cross-sectional view of the dust-proof cap showing another example.

As shown in FIG. 13, the above-mentioned cap portion 54 can form a cap 44 comprising a joint hole 44a jointing to an outer circumference of the above-mentioned cylindrical portion 258 as substitute for the above-mentioned stop 57.

In this way, the dust-proof cap 16 can certainly be protected from extraneous substance such as dust entering into the above-mentioned joint concave portion 28 during storage. As a result, it can prevent poor jointing between the air intake port 27 and the joint concave portion 28 caused by the extraneous substance and troubles such as a clogging of the air valve Tv caused by the commingling of the extraneous substance with sealing agent, and can improve reliability of the puncture repair kit 1.

In the above-mentioned puncture repair kit 1, the bottle unit 3 is a consumable supply and is replaced with respect to each puncture repairing, but the compressor device 2 is repeatedly used. Therefore, after puncture repairing, also after that the used bottle unit 3 is removed form the compressor device 2, it is necessary for the compressor device 2 to prevent the entrance of the extraneous substance into the joint concave portion 28. However, in the present embodiment, since the dust-proof cap 16 is kept by the compressor device 2, and the dust-proof cap to be missed, the compressor device 2 can be repeatedly stored cleanly.

Figure 19:
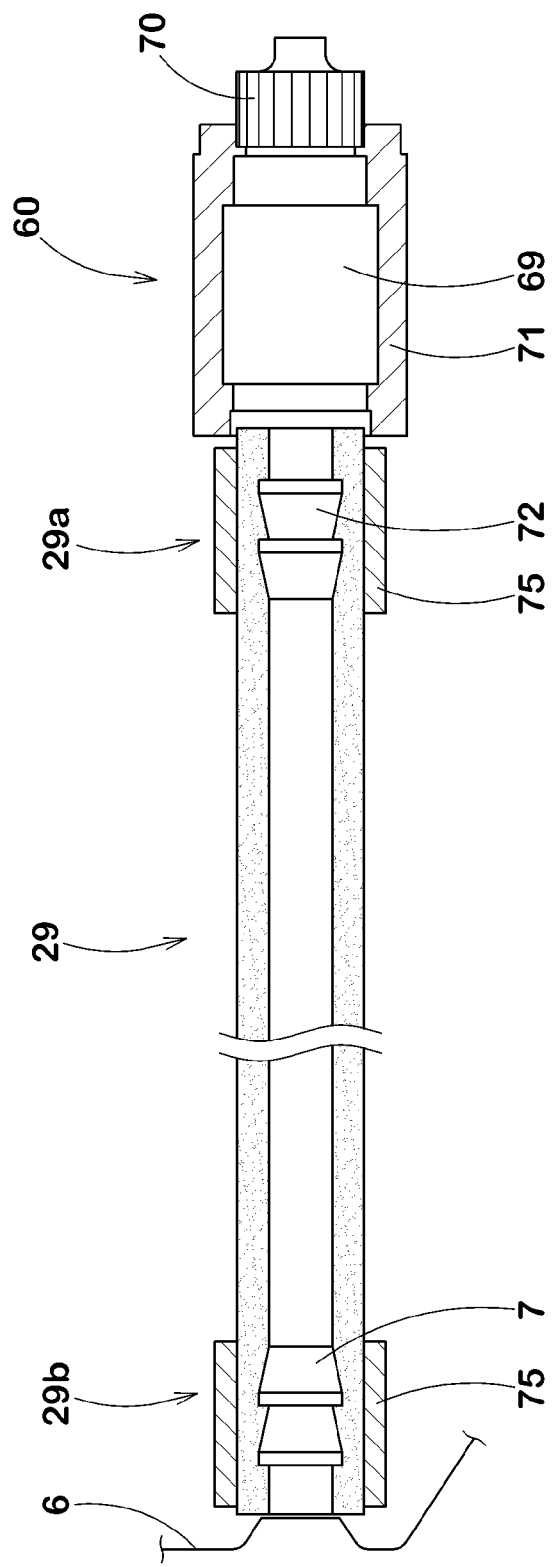
FIG. 19 A cross-sectional view in the length direction showing a feeding hose.

As shown in FIG. 19, a second end 29b of the above-mentioned feeding hose 29 is connected to the above-mentioned sealing agent/compressed air removal port 7 of the cap 6, and on a first end 29a is attached with the connector 60 enabling to connect to the air valve Tv of the tire T.

Figure 20:
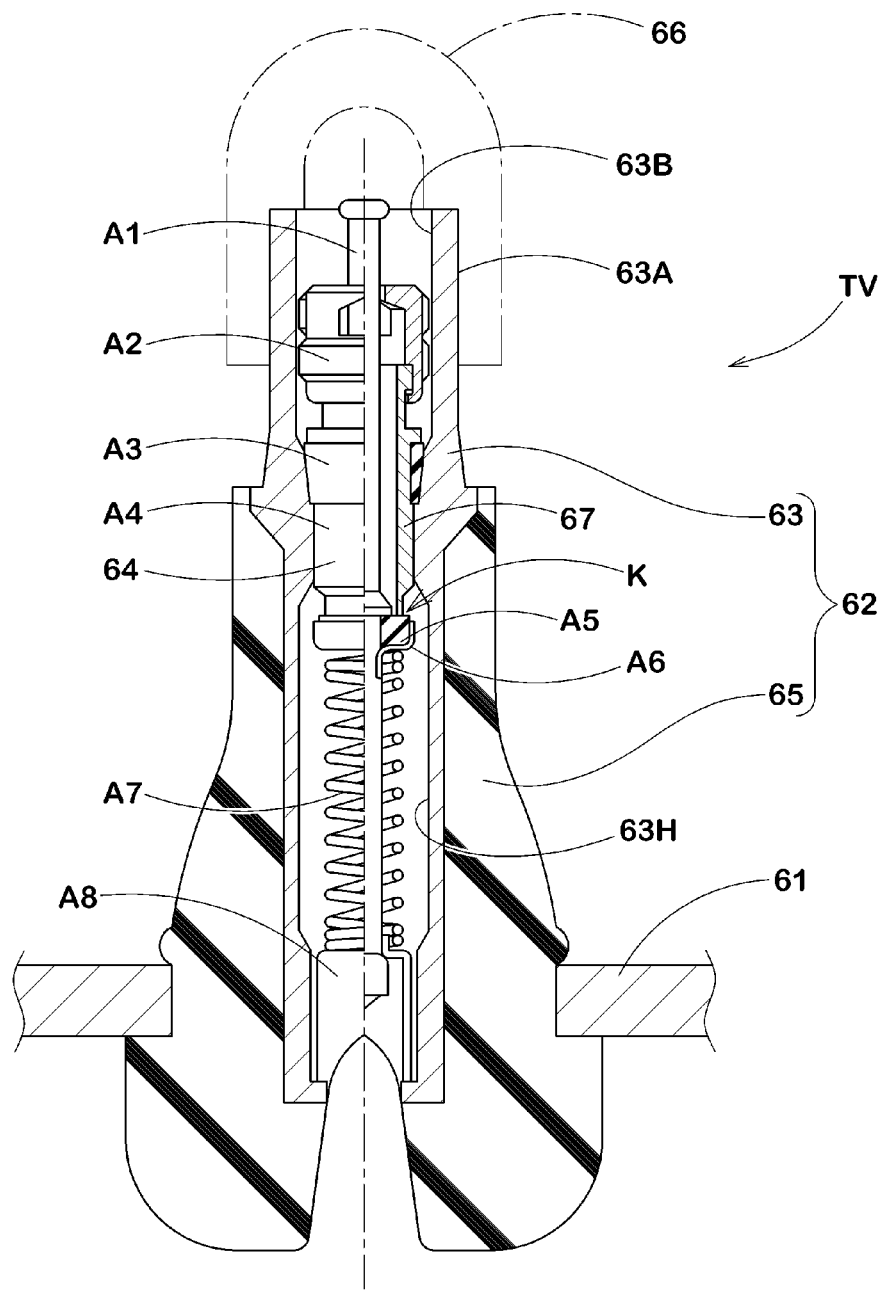
FIG. 20 A cross-sectional view of a pressure release valve of the tire.

The above-mentioned air valve Tv is a tire valve for an automobile conforming to JISD 4207 standard and the like for example; a general snap-in style is shown in FIG. 20 as an example. This air valve Tv has a well-known structure that comprises a valve stem 62 fixed to the wheel rim 61, a valve core 64 attached onto the internal bore 63H of this valve stem 62. Incidentally, the valve stem 62 comprises a rubber seat 65 attached to the wheel rim 61 and a tubular valve stem main portion 63 fixed integrally to the this rubber seat 65 in the present embodiment. An upper part of the valve stem main portion 63 is provided on an outer circumference side with an outer screw part 63A for attaching helically the valve cap 66, and on an inner circumference side with an inner screw part 63B for attaching helically the valve core 64.

The above-mentioned valve core 64 comprises a shaft A1, a head A2, a base packing A3, a trunk A4, a valve packing A5, a valve packing receiving A6, a spring A7, and a spring receiving A8 and the like. The head A2, the base packing A3, and the trunk A4 are integrally connected and formed as a unit 67, which is attached with the above-mentioned inner screw part 63B. The shaft A1, the valve packing A5, and the valve packing receiving A6 are formed integrally and retained up and down freely on the unit 67. Thus, the valve core 64 is closed with a spring A7 disposed between the above-mentioned valve packing receiving A6 and the spring receiving A8; regularly a pressure occurs for welding of a valve part K between a valve seat portion of the lower end of the trunk A4 and the valve packing A5, and these will allow to keep the tire cavity airproof. However, when filling up the tire cavity with air, the connector 60 pushes the shaft A1, and a valve seat portion of the lower end of the trunk A4 and the valve packing A5 separate, and the air is filled through the gap.

Figure 21:
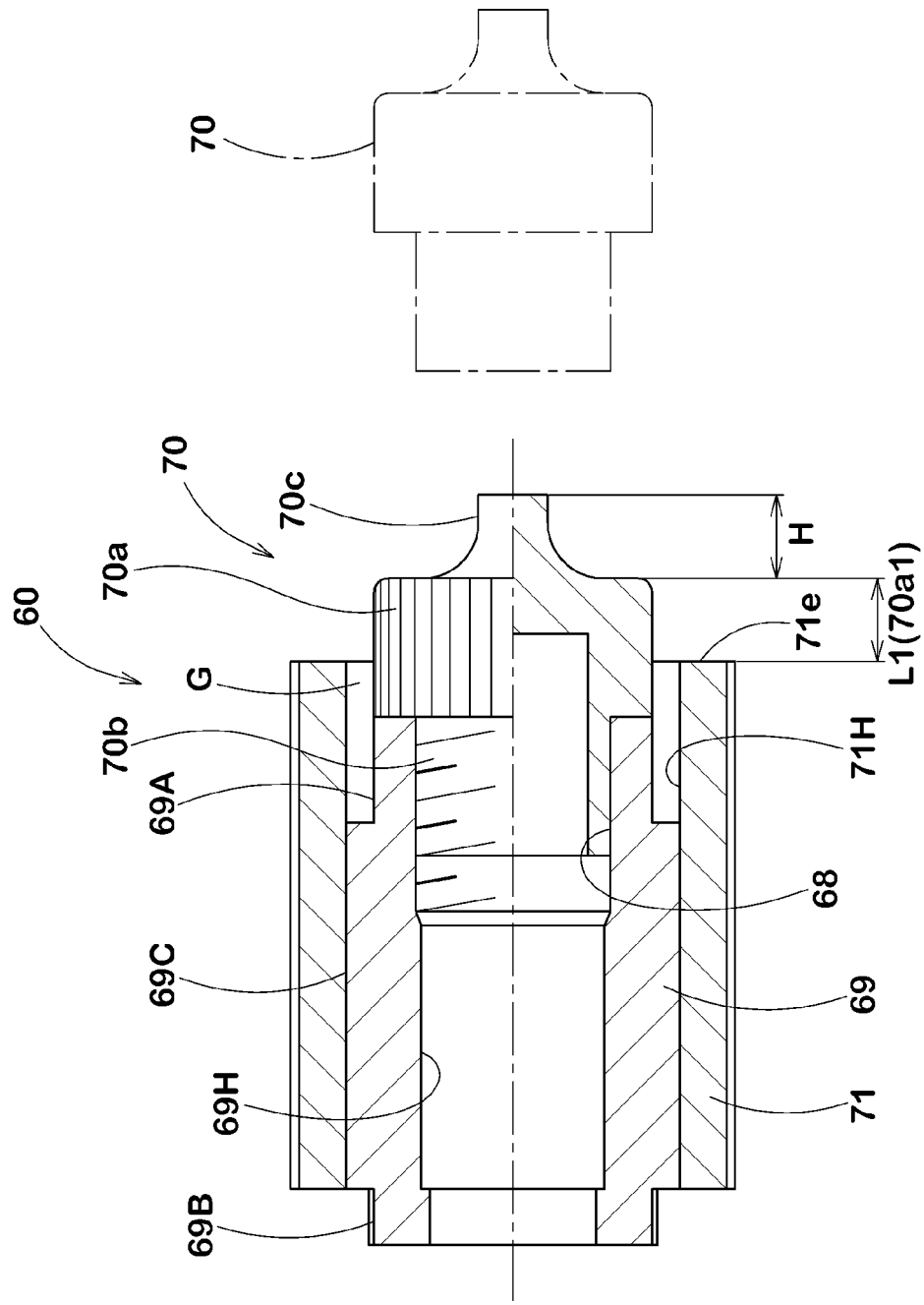
FIG. 21 A cross-sectional view of a connector of the feeding hose.

As shown in FIG. 21, the above-mentioned connector 60 of the above-mentioned feeding hose 29 comprises a cylindrical connector main portion 69 provided in the anterior end portion with a screw part 68 capable of helically attaching to an outer screw part 63A of the above-mentioned valve stem main portion 63, a closing cap 70 disposed detachably in the above-mentioned connecting screw part 68, and a cylindrical outer sleeve 71 fixed to the outer circumference of the connector main portion 69.

The above-mentioned connector main portion 69 is a stepped tubular having small-diameter sections 69A and 69B on the front or back of a large-diameter section 69C, and is provided in the internal bore 69H with the connecting screw part 68 of an inside screw type in the present embodiment.

The above-mentioned closing cap 70 comprises, a knob part 70a for turning helically in holding it between tips of fingers, and a screw part 70b disposed at a rear end of the knob part 70a and protruded via the step and fit helically with the above-mentioned connecting screw part 68.

The knob part 70a has a smaller diameter than an internal bore 71H of the above-mentioned outer sleeve 71 and sticks out beyond a tip 71e of the outer sleeve 71 by a distance L1 of at least not less than 5 mm. This protruding part 70a1 can make the above-mentioned closing cap 70 turn helically in holding it between the tips of fingers and remove it from the connector main portion 69. To make easy the above-mentioned helical turning, there is a knurling comprising a plurality of article grooves extending in the direction of shaft center around the outer circumferential surface of the knob part 70a.

Figure 22:
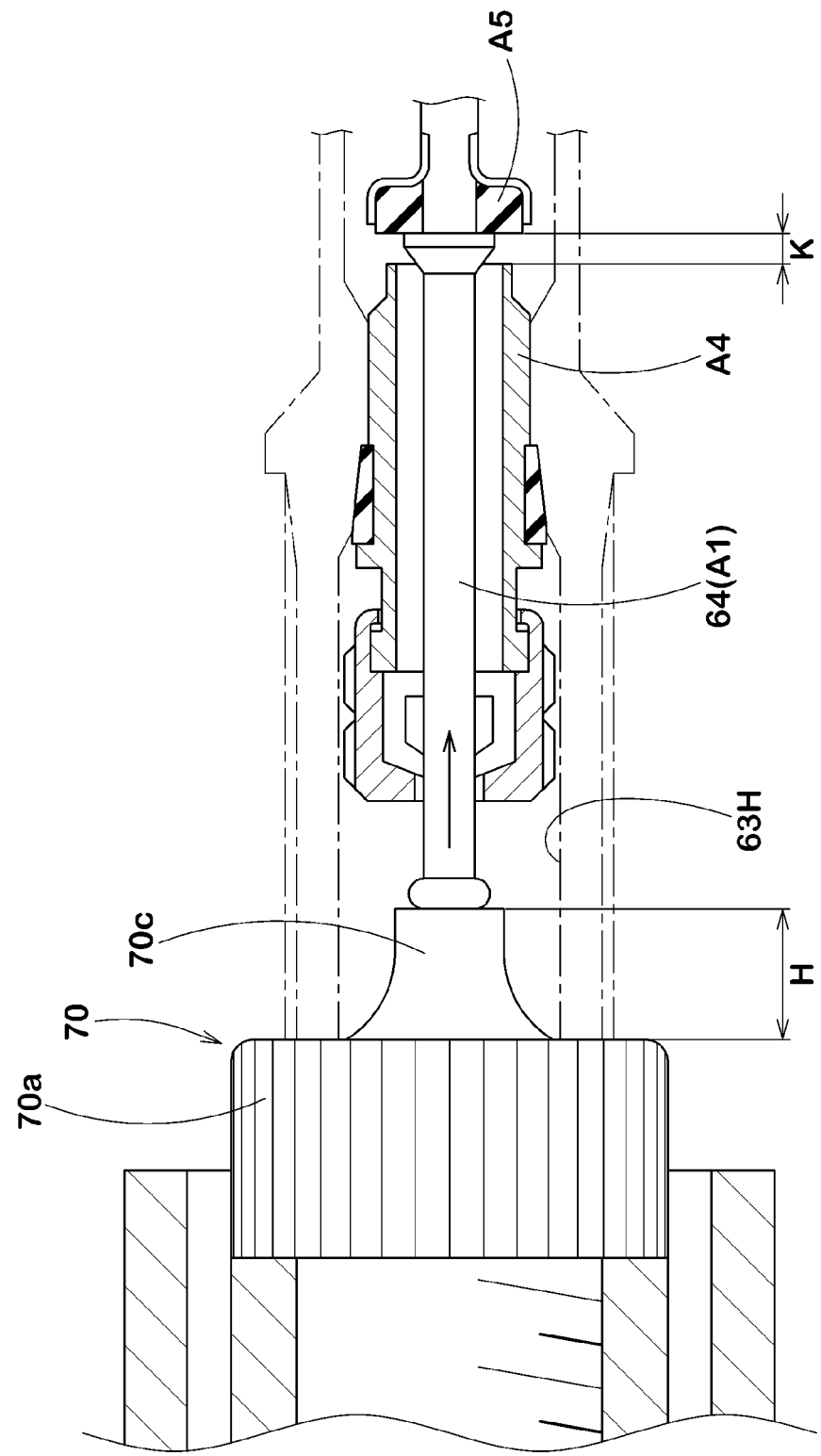
FIG. 22 A cross-sectional view showing a function of a core protruding part disposed in a closing cap.

The above-mentioned closing cap 70 is provided, in a front end of the above-mentioned knob part 70a, with the core protruding part 70c to press forward the tip of the valve core 64 of the above-mentioned air valve Tv. As shown in FIG. 22, this core protruding part 70c presses forward the tip of the valve core 64, that is to say, the tip of the shaft A1; therefore, the valve part K between the valve seat portion of the lower end of the above-mentioned trunk A4 and the above-mentioned valve packing A5 can be separate, and the air in the tire can be exhausted from the air valve Tv. Therefore, when a pressure of the tire T excessively rises by use of the puncture repair kit 1, the pressure of the tire can be reduced through the core protruding part 70c. This core protruding part 70c has a smaller diameter than an internal bore 63H of the above-mentioned valve stem main portion 63, and a protruding height H from the front end of the above-mentioned knob part 70a is preferably in a range of from 2 to 4 mm.

Figure 23:
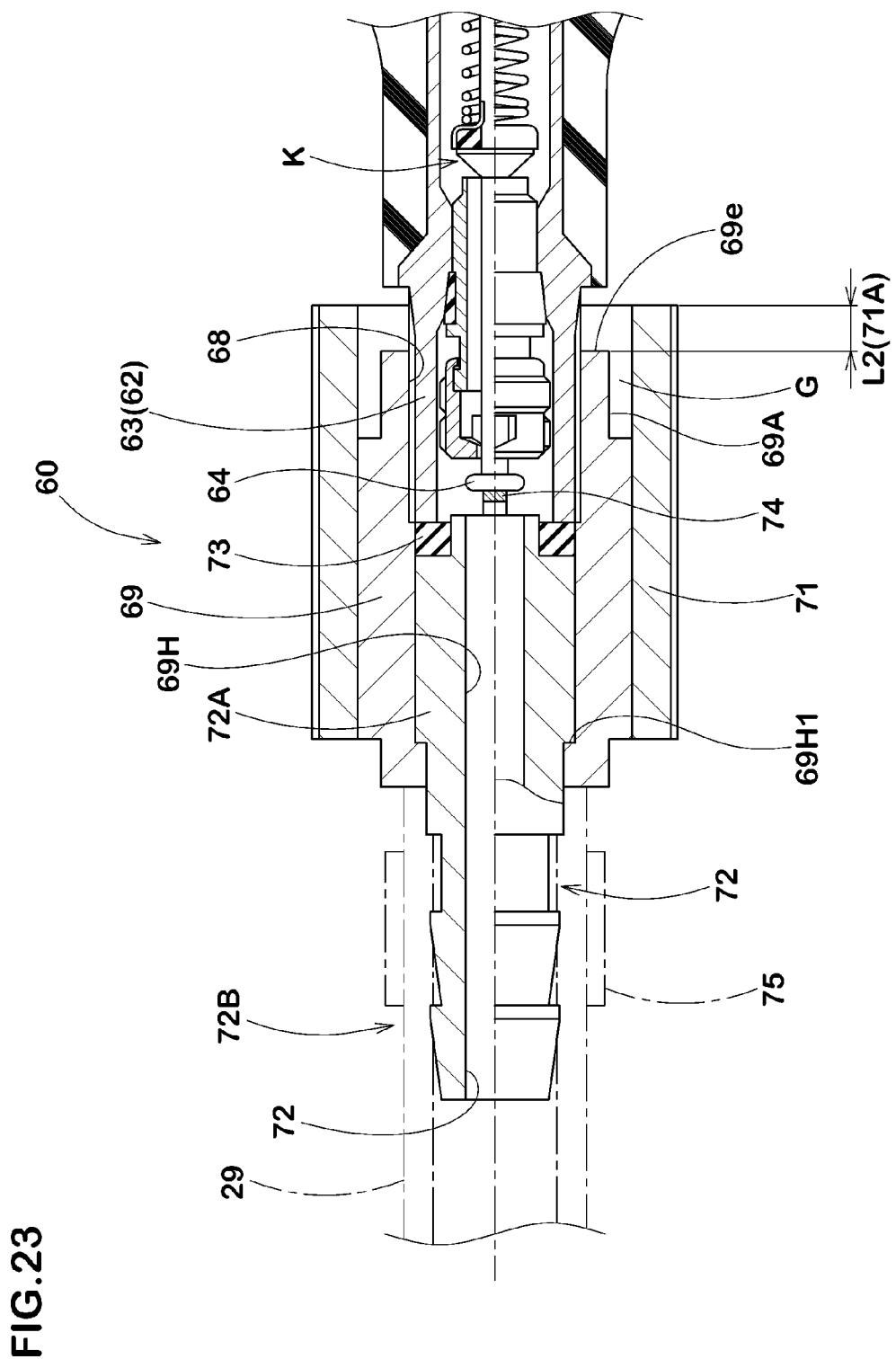
FIG. 23 A cross-sectional view showing a state of connection between the connector and the pressure release valve.

In the connector 60, as shown in FIG. 23, removing the above-mentioned closing cap 70, the above-mentioned valve stem main portion 63 can be helically attached to the above-mentioned connector main portion 69 as substitute for this closing cap 70. At this time, the above-mentioned outer sleeve 71 makes increase a thickness of the connector 60, and the operability of helical turning can be improved. This outer sleeve 71 is integrally fixed to the above-mentioned connector main portion 69 with a press fitting. And, to make the above-mentioned helical turning easier, there is the knurling on the outer circumferential surface. The outer sleeve 71 comprises a projecting portion 71A sticking out beyond the anterior end 69e of the connector main portion 69.

This projecting portion 71A serves as a shielding plate, for example; and at a time of removing the connector main portion 69 from the valve stem main portion 63 after filling up the sealing agent and the compressed air; if the sealing agent flows off from the gap between the connector main portion 69 and the valve stem main portion 63, this projecting portion 71A can prevent the sealing agent from flowing backward. Therefore, it can prevent the sealing agent from adhering to the user, and the repairing operation can be cleanly conducted. Then, a projecting quantity L2 of the above-mentioned projecting portion 71A from the anterior end 69e of the connector main portion 69 is preferably set in a range of from 1 to 5 mm. When it is less than 1.0 mm, the shielding function becomes insufficient. When it is over 5.0 mm, the applying performance to the valve stem main portion 63 decreases. In the present embodiment, there is a small-diameter section 69A on the anterior end of the above-mentioned connector main portion 69 so as to form a small gap G between the outer sleeve 71 and the small-diameter section 69A. This small gap G serves to improve the above-mentioned shielding function.

In the present embodiment, the above-mentioned connector 60 is attached to the feeding hose 29 via the tubular joint fitting 72 having the internal bore 72H connecting with the above-mentioned internal bore 69H. This joint fitting 72 comprises a trunk portion 72A inserted into the internal bore 69H of the above-mentioned connector main portion 69 and connected rotatably to the connector main portion 69, and a tapered hose joining section 72B connecting integrally to the trunk portion 72A and extending backward and capable of jointing the above-mentioned feeding hose 29, for example. The above-mentioned trunk portion 72A is retained by the interlocking with the stepped section 69H1 disposed in the internal bore 69H. And the anterior end portion of the trunk portion 72A is provided with a packing material 73 pressed and sealed between the above-mentioned valve stem main portion 63 and it, and an airproof connecting is achieved. Incidentally, a symbol 74 signifies a protrusion disposed in the anterior end portion of the trunk portion 72A; at the time of helically attaching of the valve stem main portion 63 to the connector main portion 69, the protrusion 74 pushes forward the tip of the valve core 64 and makes open the valve part K. A symbol 75 signifies a ring-like well-known hose catch to tighten and fix the feeding hose 29 to the hose joining section 72B and the sealing agent/compressed air removal port 7. The joint fitting 72 can have various conventional structures; moreover, it can be provided, in the connector main portion 69, with the hose joining section 72B without the joint fitting 72, such as directly attaching the feeding hose 29 to the connector 60.

As shown in FIGS. 24 and 25, the above-mentioned feeding hose 29 is wrapped for storage around cap 6 through intervals between the above-mentioned basal plate 31 and the bottle container 4 while keeping the connection to the above-mentioned sealing agent/compressed air removal port 7 during storage. This feeding hose 29 is not less than 50 cm, between from 50 to 60 cm in this example, and is wrapped 2.5 times around the above-mentioned cap 6.

For details, the feeding hose 29 is wrapped through intervals between the above-mentioned air intake port 27 and the upper locking click 45 and between the air intake port 27 and the lower locking click 45 respectively while intersecting with each other, and prevented from rewinding by a rewinding-preventing plate portion 80 comprised in the cap 6. More particularly, the rewinding-preventing plate portion 80 is a plate-like portion protruding radially from a side wall of the above-mentioned bottle attaching part 32 as shown in FIG. 9. At its central, there is a rewinding-preventing hole 80H provided to insert the above-mentioned connector 60. This rewinding-preventing plate portion 80 is secured onto the rewinding-preventing hole 80H by a resilience of the feeding hose 29 form a bended deformation so as to prevent the rewinding. Incidentally, the side wall of the bottle attaching part 32 is provided with a low height guide rib 81 extending in the circumferential direction to lead the feeding hose 29 into the above-mentioned rewinding-preventing hole 80H.

In this way, the waist part 33 of the above-mentioned cap 6 is defined as a twisted small diameter, and the side wall of the above-mentioned bottle attaching part 32 is provided with a rewinding-preventing plate portion 80 in a protruding condition. Thus, the above-mentioned feeding hose 29 can be wrapped around the waist part 33, thereby having the small diameter compactly. And, a first end of the connector 60 of the wrapped feeding hose 29 is prevented to be rewind by the winding-preventing plate portion 80; therefore, a space-saving winding can be achieved, and its storage can be space-saving.

The rewinding-preventing plate portion 80 is formed at a position of facing parallely to the above-mentioned side plate 14a1 at the time of connection between the compressor device 2 and the bottle unit 3. And, the above-mentioned side plate 14a1 is provided in a protruding condition with a shifting-proof convex portion 83 to prevent a shifting at the time of connection with the rewinding-preventing hole 80H (shown in FIGS. 1 and 2).

A thickness and a length of the above-mentioned feeding hose 29 are determined not to be over an outer peripheral edge of the above-mentioned bottle trunk portion 30 or the above-mentioned circumscribed cuboid 50 at a time of wrapping. In the bottle unit 3, the above-mentioned boss portion 32B is jointed with an inner stopper 52 closing the air flow passage upper opening 37 and the sealing agent/compressed air removal flow passage upper opening 38 respectively to prevent from an outflow of the puncture sealing agent in the bottle container 4 at an unoccupied time as shown in FIG. 8 with a dashed-dotted line. This inner stopper 52 can come off from boss portion 32B by a pressure rise by the compressed air from the compressor device 2.

A puncture repair kit 1 according to the second embodiment is shown in FIGS. 26 to 30. In the puncture repair kit 1 of the second embodiment, the securing device 34 is formed in the above-mentioned basal plate 31, and is provided with the locking device 34A comprising a pair of locking clicks 95 projecting on the both sides in the outward widthwise direction and being deformable elastically in the inward widthwise direction.

Figure 29:
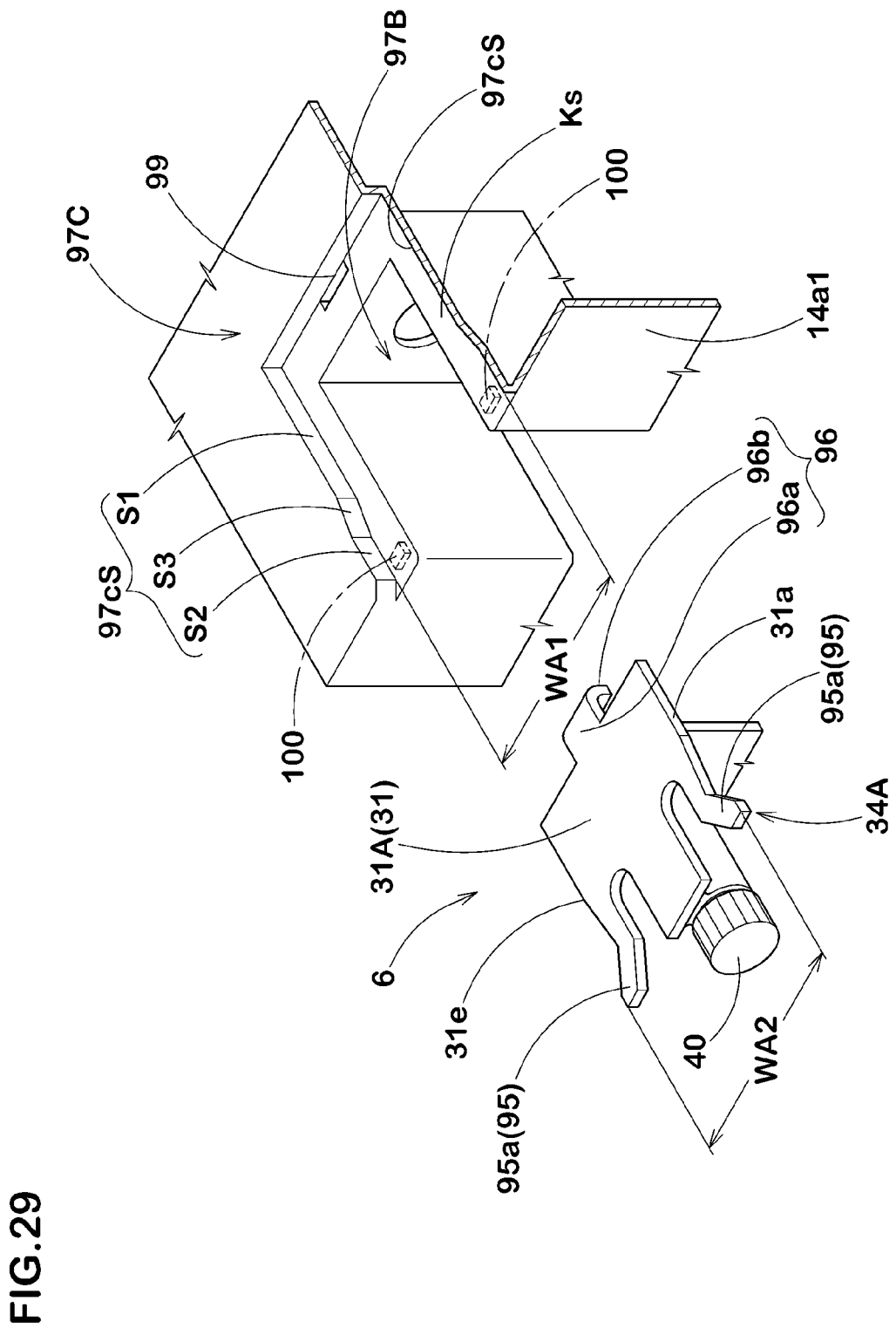
FIG. 29 A partial perspective view from underneath showing a basal plate and a basal-plate-receiving concave portion at a previous state of connecting.
Figure 30:
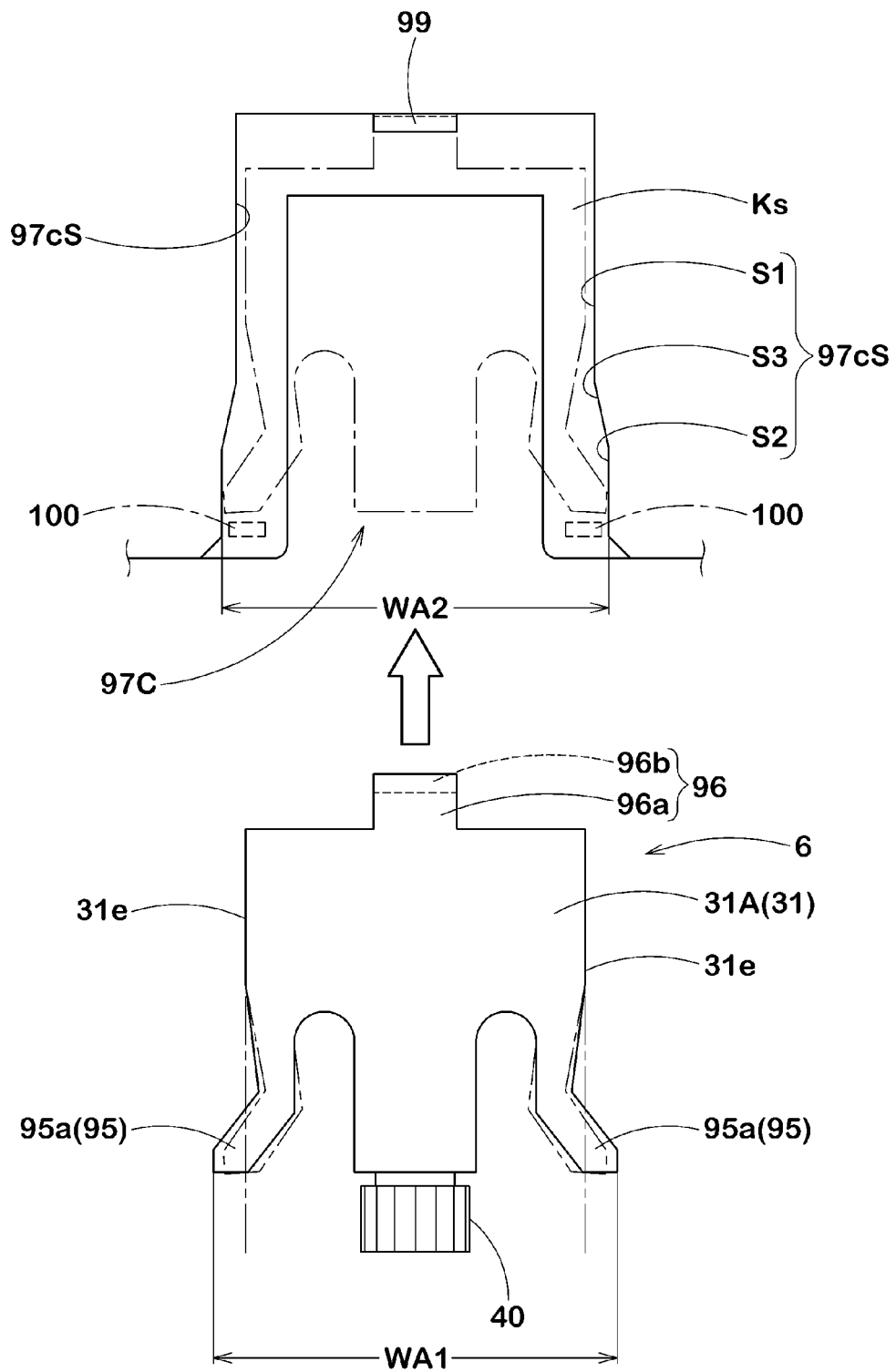
FIG. 30 A figure explaining from underneath the connection between the basal plate and the basal-plate-receiving concave portion with a securing device.

More particularly, as shown in FIGS. 29 and 30 as viewed from the basal plane side, the above-mentioned basal plate 31 comprises a rectangle plate-like board portion 31A, and the above-mentioned pair of the locking clicks 95 is provided with projecting portion 95a extending outward from over the side edge 31e of the board portion 31A on the both sides in the widthwise direction. In the present embodiment, the above-mentioned locking click 95 is formed of an elastically-deformable tip inflected in a substantially "<"-like fashion (include a curvature) and extends toward outside from the board portion 31A. A rear end portion of this tip forms the above-mentioned projecting portion 95a projecting outward on the both sides in the widthwise direction.

The above-mentioned locking device 34A comprises an anterior locking click 96 protruding from an anterior end of the above-mentioned board portion 31A and being deformable elastically up and down. The anterior locking click 96 is provided with a hooking part 96b projected upward in the anterior end of the plate-like main part 96a extending forward from the board portion 31A.

Figure 26:
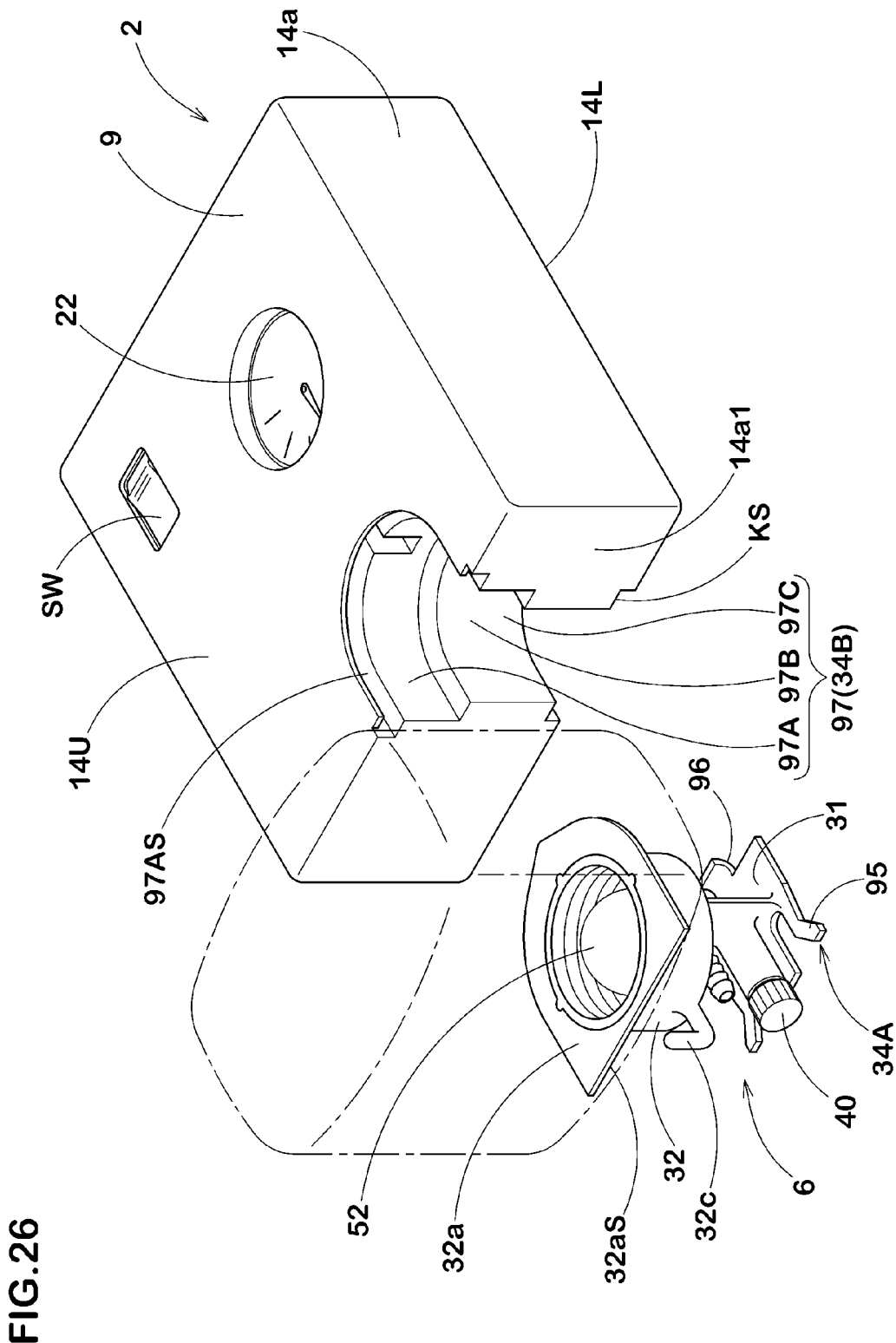
FIG. 26 A perspective view of the puncture repair kit showing another example.
Figure 27:
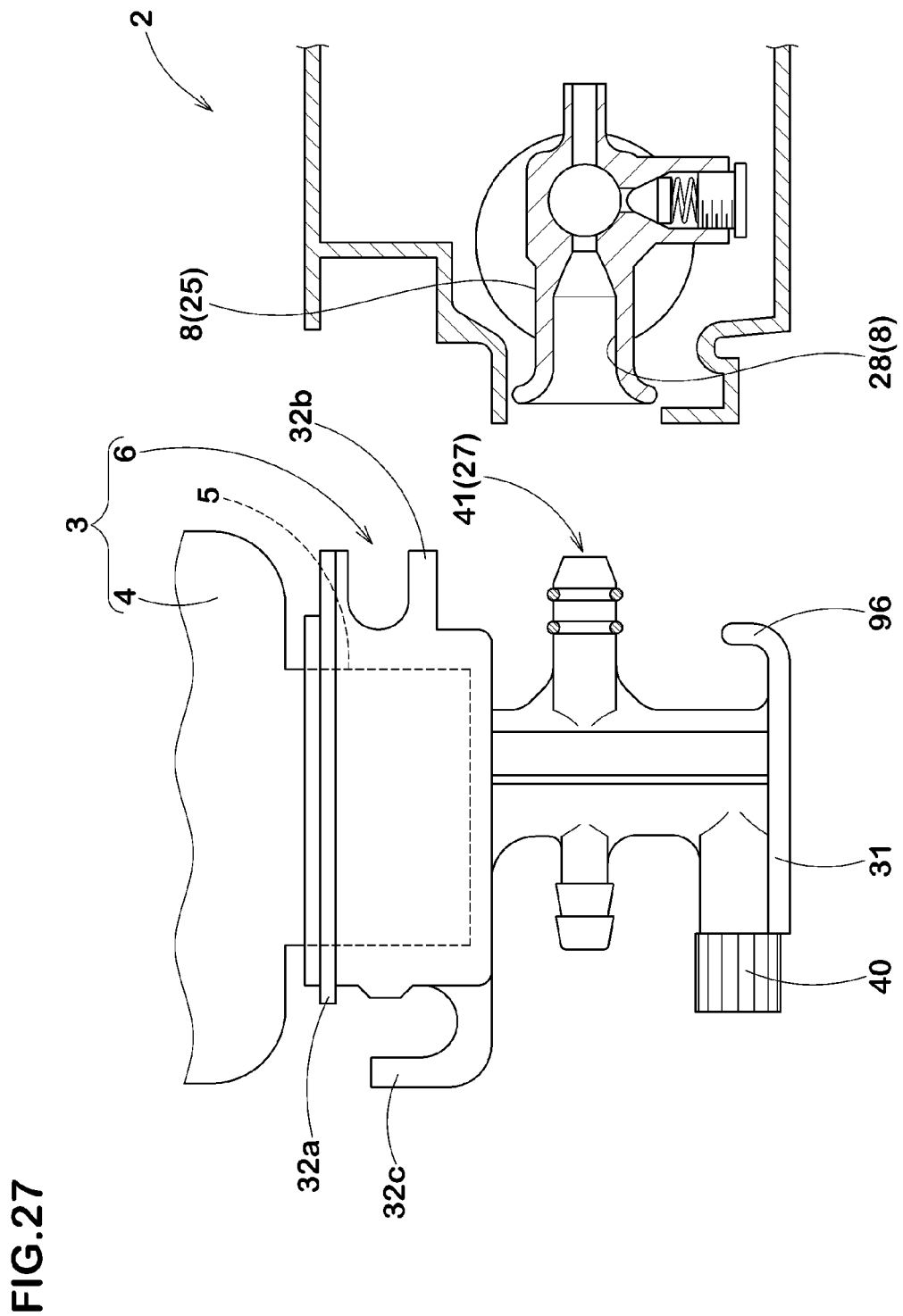
FIG. 27 A cross-sectional view of the securing device showing a state before directly connecting.
Figure 28:
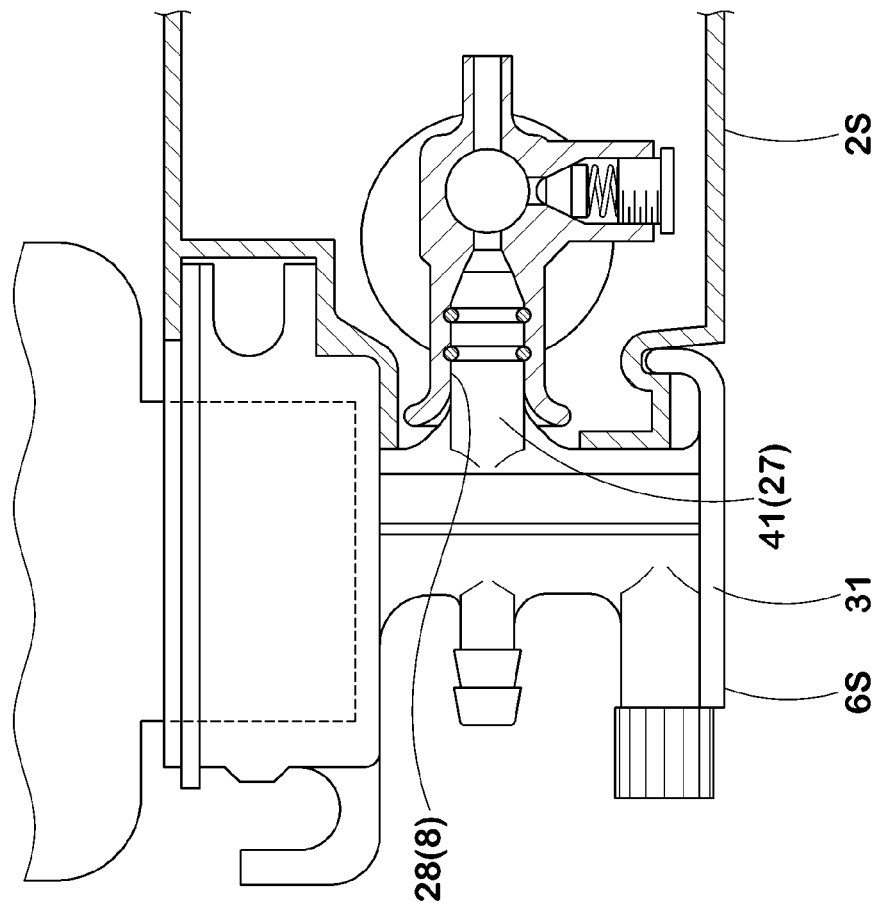
FIG. 28 A cross-sectional view of the securing device showing in a directly connecting state.

As shown in FIG. 26, on the first side surface 14a1 of the above-mentioned compressor device 2, the interlocking device 34B comprising a substantially-semicircle concave portion 97, which fits with the outer surface shape of the above-mentioned cap 6 and receives the cap 6 to be seated in the above-mentioned directly connecting state, is formed.

This receiving concave portion 97 comprises
a bottle-receiving concave portion 97A to receive the above-mentioned bottle attaching part 32,
a waist-part-receiving concave portion 97B to receive the above-mentioned waist part 33, and
a basal-plate-receiving concave portion 97C to receive the above-mentioned basal plate 31. The bottle-receiving concave portion 97A comprises a guide part 97AS to lead the flange portion 32a disposed in the upper end of the bottle attaching part 32, and the above-mentioned air intake port 27 is accurately led to the above-mentioned compressed air discharge port 8 at the time of connecting the bottle unit 3.

The above-mentioned basal-plate-receiving concave portion 97C receives the above-mentioned basal plate 31 by deforming elastically the above-mentioned locking click 95 in the inward widthwise direction between these side walls 97cS and 97cS as shown in FIGS. 29 and 30. The side wall 97cS comprises
a first side wall part S1 extending along the side edge 31e of the above-mentioned board portion 31A,
a second side wall part S2 receiving the above-mentioned locking click 95, and
a sloping surface part S3 connecting between the first side wall part S1 and the second side wall part S2.
A width WA1 between the side wall parts S2 and S2 is smaller than a width WA2 between the before-inserting locking click 95 and 95. Owing to its difference (WA2−WA1), the basal plate 31 can be received with elastic deformation of the locking click 95 inward in the widthwise direction.

In said directly connecting state, the above-mentioned basal-plate-receiving concave portion 97C is provided, at a position of facing the above-mentioned anterior locking click 96), with a locking portion 99 to prevent the above-mentioned cap 6 from falling out from concave portion 97 by interlocking up-and-down with the above-mentioned hooking part 96b of the anterior locking click 96.

The above-mentioned basal-plate-receiving concave portion 97C can be provided with an interlocking protrusion 100 (shown in FIGS. 29 and 30 with a dashed-dotted line) for fall-out prevention of the above-mentioned cap 6 by interlocking with the posterior end of the above-mentioned locking click 95. In this case, the anterior locking click 96 and the locking portion 99 can be removed. The above-mentioned anterior locking click 96 and its locking portion 99 can be used in combination. The interlocking protrusion 100 can protrude with a small height on the above-mentioned side wall 97cS, also can protrude with a small height on a step surface KS between the above-mentioned waist-part-receiving concave portion 97B and the basal-plate-receiving concave portion 97C as shown in this example.

Figure 31:
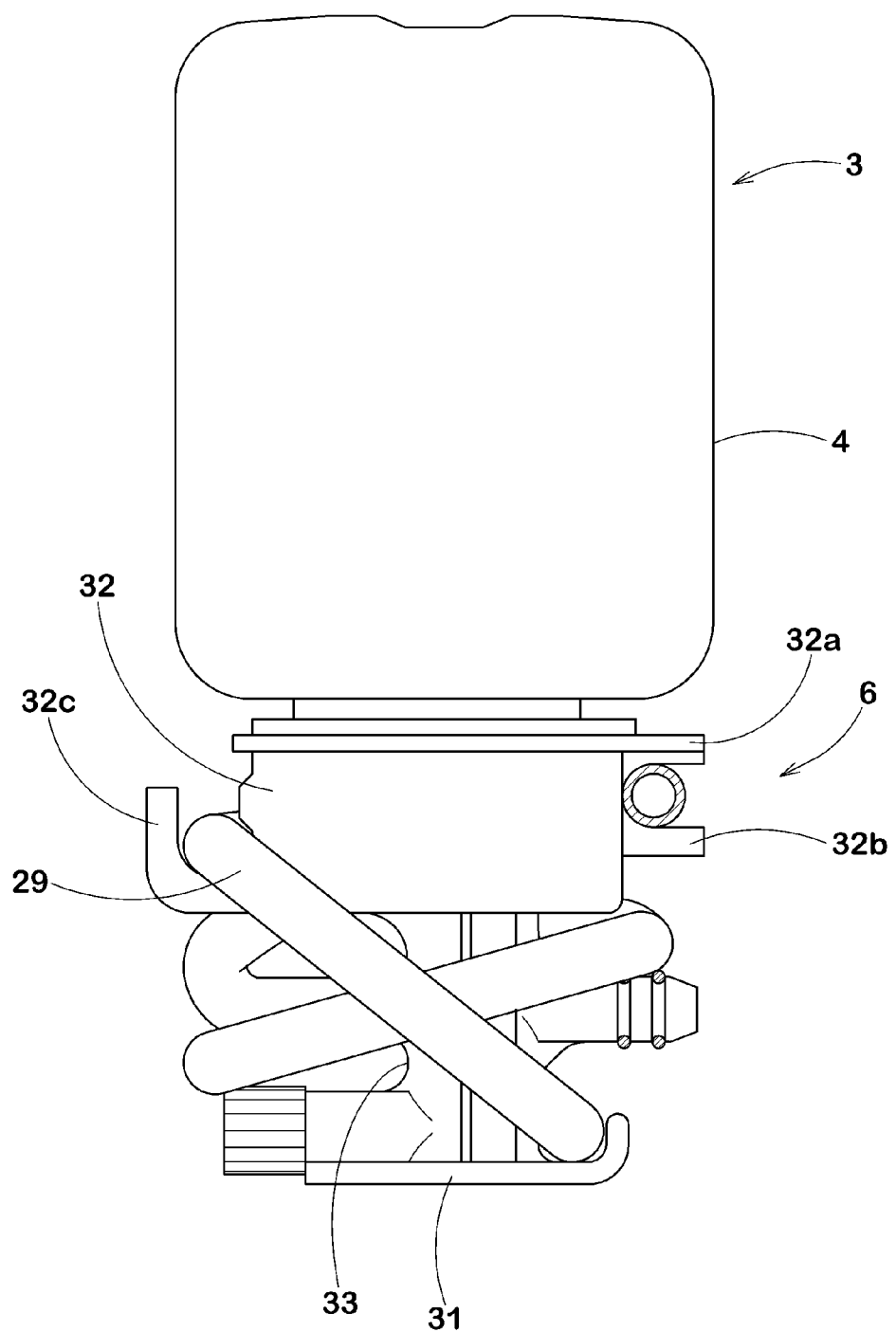
FIG. 31 A side view showing a storage state of the feeding hose.
Figure 32:
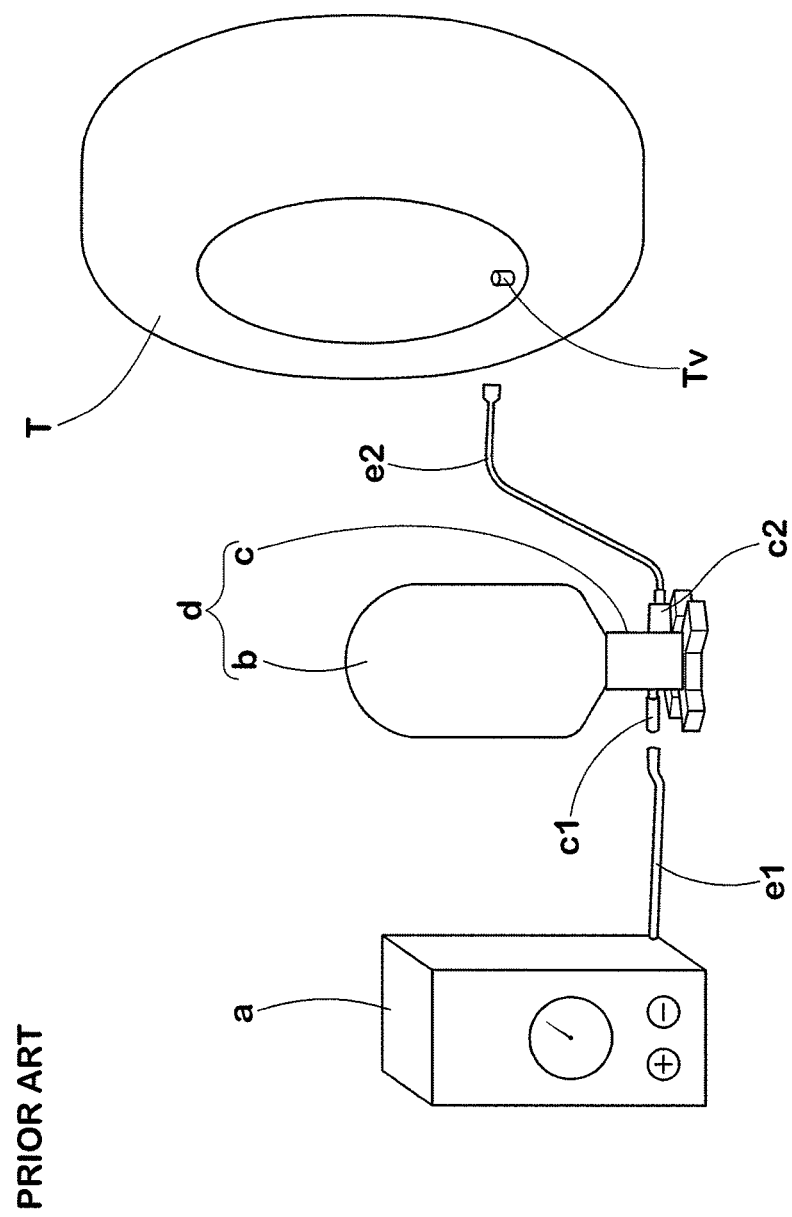
FIG. 32 A perspective view explaining a conventional puncture repair kit.

In the present embodiment, the above-mentioned bottle attaching part 32 is provided with anterior and posterior hose retaining tips 32b and 32c comprising a retaining hole to retaining the feeding hose 29 wrapped around the cap 6 during storage as shown in FIG. 31. In the present embodiment, the above-mentioned sealing agent container 39 is closed with the container portion over 40 provided in the above-mentioned waist part 33.

Although the especially preferred embodiments of the present invention have been described in detail, the invention is not limited to the illustrated embodiments, and various modifications can be made.

EXAMPLE

In a puncture repair kit in the present invention, a bottle container having a cross sectional shape shown in FIG. 14, is made by way of test based on a specification shown in Table 1 to compare magnitudes of change of the cross sectional shape under internal pressure load of 400 kPa on this bottle container. The specification other than Table 1 is substantially the same.

<Common Specification of Bottle Container>
 Material: polypropylene
 Thickness: 2.1 mm
 Height of bottle: 80 mm
 Curvature of corner portion: 10 mm In this test, an expanse amount on a long side at the time of loading the internal pressure of 400 kPa on the bottle container is resulted. When the expanse amount is over 7 mm, a user feels a deep sense of unease that the bottle container is about to burst. Therefore, the above-mentioned expanse amount of not more than 7 mm shall pass the test.

TABLE 1

| <Bottle container> | Example 1 | Example 2 | Example 3 | Example 4 | Example 5 | Example 6 | Example 7 | Example 8 | Example 9 |
| --- | --- | --- | --- | --- | --- | --- | --- | --- | --- |
| Cross sectional shape | round | substantial rectangle | substantial rectangle | substantial rectangle | substantial rectangle | substantial rectangle | substantial rectangle | substantial rectangle | substantial rectangle |
| Long side part | straight line | convex arc | convex arc | convex arc | convex arc | convex arc | convex arc | convex arc | convex arc |
| Length W <mm> | 70 | 129 | 96 | 100 | 110 | 106 | 110 | 100 | 92 |
| Radius of curvature RW <mm> | 35 | 1500 | 150 | 110 | 79.5 | 150 | 150 | 350 | 250 |
| Short side part | straight line | convex arc | convex arc | convex arc | convex arc | convex arc | convex arc | convex arc | convex arc |
| Length D <mm> | 70 | 67 | 70 | 70 | 70 | 70 | 65 | 70 | 70 |
| Radius of curvature RD <mm> | 35 | 1000 | 1000 | 1000 | 1000 | 120 | 150 | 1000 | 1500 |
| Ratio W/D | 1.0 | 1.93 | 1.37 | 1.43 | 1.57 | 1.51 | 1.69 | 1.43 | 1.31 |
| Ratio RW/W | 0.5 | 11.63 | 1.56 | 1.10 | 0.72 | 1.42 | 1.36 | 3.50 | 2.72 |
| Ratio RD/D | 0.5 | 14.93 | 14.29 | 14.29 | 14.29 | 1.71 | 2.31 | 14.29 | 21.43 |
| Expanse amount on long side <mm> | 1.5 (passed) | 18 (rejected) | 6 (passed) | 5 (passed) | 3.5 (passed) | 6.5 (passed) | 7 (passed) | 8 (rejected) | 8.5 (rejected) |

As shown in Table 1, the expanse amount on the long side is not more than 7 mm, small, in the bottle container according to Examples 3 to 7 that meet the following conditions (1) to (3) among Examples 1 to 9:

$$1.3 \leq W/D \leq 1.7 \tag{1}$$

$$0.5 \leq RW/W \leq 3.0 \tag{2}$$

$$0.5 \leq RD/D \leq 20.0 \tag{3}$$

Therefore, it is confirmed that it reduces the unease feeling that the bottle container is about to burst.

The invention claimed is:

1. A puncture repair kit comprising:
a compressor device containing in a housing:
  a motor; and
  a compressor main body comprising:
    a piston connected to the motor via a crank mechanism, and
    a cylinder reciprocatingly enclosing the piston and forming a pump chamber to compress the air between the cylinder and the piston; and
a bottle unit comprising:
  a bottle container enclosing puncture sealing agent; and
  a cap attached to an opening of the bottle container;
wherein:
  said compressor device comprises
    a compressed air discharge port formed on said cylinder in a protruding condition, and disposed on a first side surface of the compressor device for discharging compressed air;
  said cap comprises
    an air intake port to intake the compressed air from said compressed air discharge port into the bottle container, and
    a sealing agent/compressed air removal port to remove in succession the puncture sealing agent and the compressed air from said bottle container by sending the compressed air; and
  said compressor device has a shape of a flat rectangular box;
  said air intake port of said bottle unit is directly connected with said compressed air discharge port without any hoses intervention in an inverted state with the cap faced downward; and
  in said directly connecting state, a basal plane of said cap and a basal plane of the compressor device are flush with each other so as to make a ground contact surface.

2. The puncture repair kit as set forth in claim 1, wherein a width at right angle to said first side surface of said basal plane of said cap is substantially equivalent to a width at right angle to said first side surface of said bottle container.

3. The puncture repair kit as set forth in claim 1, wherein lengths of two sides among three sides of a bottle-side circumscribed cuboid circumscribed by a surface of a bottle unit is set to be equal to lengths of two sides among three sides of a compressor-side circumscribed cuboid circumscribed by a surface of said compressor device.

4. The puncture repair kit as set forth in claim 1, wherein
said bottle container comprises a trunk portion of which cross-section perpendicular to the height direction of the bottle container is a substantially rectangular shape surrounded with a pair of long side parts curved in convex arc toward an outside of the bottle, and a pair of short side parts curved in convex arc; and
when
a length of said long side part is defined as W,
a radius of curvature of the long side part is defined as RW,
a length of said short side part is defined as D, and
a radius of curvature of the short side part is defined as RD
in the present embodiment, they meet the following relations (1)-(3):

$$1.3 \leq W/D \leq 1.7 \tag{1}$$

$$0.5 \leq RW/W \leq 3.0 \tag{2}$$

$$0.5 \leq RD/D \leq 20.0 \tag{3}$$

5. The puncture repair kit as set forth in claim 1, wherein
said air intake port comprises a connecting nozzle, and
said compressed air discharge port is provided with a cylindrical portion which extends from said cylinder in penetrating said housing outward and with an opened outlet port to extrude the compressed air at the end of the cylindrical portion;
the central hole of the cylindrical portion forms a joint concave portion directly connecting said connecting nozzle; and
said compressor device is provided with a dust-proof cap capable of being attached and removed to said outlet port, and the dust-proof cap attached to the outlet port prevents an entry of a foreign substance into said joint concave portion during storage.

6. The puncture repair kit as set forth in claim 5, wherein said dust-proof cap comprises a cap portion to close said outlet port,
a ring securing part outserted in said cylindrical portion, and
a bendable joining section connecting between said cap portion and said ring securing part.

7. The puncture repair kit as set forth in claim 1, wherein said cap comprises an air flow passage to send the compressed air of said compressor device from the air intake port into the bottle container and a sealing agent/compressed air removal flow passage to remove puncture sealing agent and the compressed air from said bottle container;
said cap comprises an attaching concave part to fix the opening of the bottle container and a boss portion rising from a basal plane of the attaching concave part, and
a top surface of said boss portion is provided with an air flow passage upper opening where a top end of said air flow passage opens and a sealing agent/compressed air removal flow passage upper opening where a top end of said sealing agent/compressed air removal flow passage opens;
said air flow passage comprises a vertical air flow passage extending inferiorly from said air flow passage upper opening and a horizontal air flow passage intersecting with the vertical air flow passage at right angle at an intersection point P and extending from the intersection point P to said air intake port; and
a sealing agent container is provided in a lower end part of said vertical air flow passage, said sealing agent container taking in the flowing backward puncture sealing agent when the puncture sealing agent flows backward from the air flow passage upper opening.

8. The puncture repair kit as set forth in claim 7, wherein an upper end of said air flow passage is higher than an upper end of said sealing agent/compressed air removal flow passage.

9. The puncture repair kit as set forth in claim 7, wherein said vertical air flow passage is provided on its upper end side with a squeezing part for reducing the inside diameter, and an inside diameter of said air flow passage upper opening is set between 1.0 and 2.0 mm.

10. The puncture repair kit as set forth in claim 7, wherein an inside diameter of said vertical air flow passage at the position of said intersection point P is set to be larger than an inside diameter of said horizontal air flow passage at the position of said intersection point P.

11. The puncture repair kit as set forth in claim 1, wherein said cap comprises
a basal plate forming the basal plane,
a bottle attaching part to attach the opening of said bottle container, and
a waist part disposed therebetween, and
said waist part provided with said air intake port and said sealing agent/compressed air removal port in a protruding condition;
said sealing agent/compressed air removal port is connected with a second end of a feeding hose of which a first end is attached to a connector connectable with an air valve of a tire;
said feeding hose is wrapped between said basal plate and the bottle container and around the cap to store it; and
said cap is provided with a rewinding-preventing plate portion protruding from the side wall of said bottle attaching part and having a rewinding-preventing hole to prevent rewinding of the feeding hose by insertion of said connector.

12. The puncture repair kit as set forth in claim 11, wherein
said cap is provide in a protruding condition on the top and bottom of said air intake port with locking clicks to be fixed to said compressor device; and
said feeding hose is wrapped around the cap through intervals between said air intake port and an upper locking click and between the air intake port and a lower locking click.

13. The puncture repair kit as set forth in claim 11, wherein said cap is on a side wall of said bottle attaching part provided with a guide rib extending in the circumferential direction to guide said feeding hose into said rewinding-preventing hole.

14. The puncture repair kit as set forth in claim 1, wherein said cap comprises
a basal plate forming the basal plane,
a bottle attaching part to attach the opening of said bottle container, and
a waist part disposed therebetween, and
said waist part provided with said air intake port and said sealing agent/compressed air removal port;
said cap is provided in said basal plate with a locking device comprising a pair of locking clicks extending toward both outer sides in the widthwise direction and being elastically deformable inward in the widthwise direction; and
said compressor device is provided with a concave portion which receives the basal plate while elastically deforming the locking clicks inside in the widthwise direction so as to fix said bottle unit to the compressor device in said directly connecting state.

15. The puncture repair kit as set forth in claim 14, wherein said basal plate comprises a rectangle plate-like board portion, and
said pair of locking clicks is provided with a projecting portion extending from a posterior end of said board portion with over the side edge of the board portion on the both sides in the widthwise direction.

16. The puncture repair kit as set forth in claim 15, wherein said locking device comprises
said pair of locking clicks and
an anterior locking click protruding from an anterior end of said board portion and being deformable elastically up and down,
said basal-plate-receiving concave portion is provided, at a position facing to said anterior locking click in said directly connecting state, with a locking portion to prevent from falling out from said compressed air discharge port of said air intake port by up-and-down interlocking with the anterior locking click.

17. The puncture repair kit as set forth in claim 2, wherein lengths of two sides among three sides of a bottle-side circumscribed cuboid circumscribed by a surface of the bottle unit is set to be equal to lengths of two sides among three sides of a compressor-side circumscribed cuboid circumscribed by a surface of said compressor device.

18. The puncture repair kit as set forth in claim 2, wherein
said bottle container comprises a trunk portion of which cross-section perpendicular to the height direction of the bottle container is a substantially rectangular shape surrounded with a pair of long side parts curved in convex arc toward an outside of the bottle, and a pair of short side parts curved in convex arc; and
when
a length of said long side part is defined as W,
a radius of curvature of the long side part is defined as RW,
a length of said short side part is defined as D, and a radius of curvature of the short side part is defined as RD in the present embodiment, they meet the following relations (1)-(3):

$$1.3 \leq W/D \leq 1.7 \quad (1)$$

$$0.5 \leq RW/W \leq 3.0 \quad (2)$$

$$0.5 \leq RD/D \leq 20.0 \quad (3).$$

19. The puncture repair kit as set forth in claim 3, wherein said bottle container comprises a trunk portion of which cross-section perpendicular to the height direction of the bottle container is a substantially rectangular shape surrounded with a pair of long side parts curved in convex arc toward an outside of the bottle, and a pair of short side parts curved in convex arc; and when
a length of said long side part is defined as W,
a radius of curvature of the long side part is defined as RW,
a length of said short side part is defined as D, and
a radius of curvature of the short side part is defined as RD in the present embodiment, they meet the following relations (1)-(3):

$$1.3 \leq W/D \leq 1.7 \quad (1)$$

$$0.5 \leq RW/W \leq 3.0 \quad (2)$$

$$0.5 \leq RD/D \leq 20.0 \quad (3).$$

20. The puncture repair kit as set forth in claim 8, wherein said vertical air flow passage is provided on its upper end side with a squeezing part for reducing the inside diameter, and an inside diameter of said air flow passage upper opening is set between 1.0 and 2.0 mm.

* * * * *